(12) United States Patent
Riley et al.

(10) Patent No.: US 8,225,639 B2
(45) Date of Patent: Jul. 24, 2012

(54) UNIVERSAL AIR BUBBLE DETECTOR

(75) Inventors: Timothy A. Riley, Salt Lake City, UT (US); Mark D. Stringham, Salt Lake City, UT (US); David H. Blaine, Salt Lake City, UT (US); Frank A. Crandall, Salt Lake City, UT (US); Philip N. Eggers, Salt Lake City, UT (US)

(73) Assignee: Zevex, Inc., Salt Lake City, UT (US)

( * ) Notice: Subject to any disclaimer, the term of this patent is extended or adjusted under 35 U.S.C. 154(b) by 0 days.

(21) Appl. No.: 12/911,690

(22) Filed: Oct. 25, 2010

(65) Prior Publication Data

US 2011/0036143 A1    Feb. 17, 2011

Related U.S. Application Data

(60) Continuation of application No. 12/487,611, filed on Jun. 18, 2009, now Pat. No. 7,818,992, which is a division of application No. 11/876,609, filed on Oct. 22, 2007, now Pat. No. 7,726,174.

(60) Provisional application No. 60/862,750, filed on Oct. 24, 2006, provisional application No. 60/949,417, filed on Jul. 12, 2007.

(51) Int. Cl.
*G01N 29/00* (2006.01)
(52) U.S. Cl. ...................................... 73/19.03
(58) Field of Classification Search .................. None
See application file for complete search history.

(56) References Cited

U.S. PATENT DOCUMENTS

| | | |
|---|---|---|
| 3,090,222 A | 5/1963 | Akaboshi et al. |
| 3,450,476 A | 6/1969 | Rando |
| 3,974,681 A | 8/1976 | Namery |
| 3,987,674 A | 10/1976 | Baumoel |
| 3,994,599 A | 11/1976 | Southwell |
| 4,054,255 A | 10/1977 | Magenheim |
| 4,068,521 A | 1/1978 | Cosentino et al. |
| 4,277,711 A | 7/1981 | Hanafy |
| 4,312,341 A | 1/1982 | Zissimopoulos et al. |
| 4,399,362 A | 8/1983 | Cormier et al. |
| 4,492,463 A | 1/1985 | Marcuse et al. |
| 4,559,454 A | 12/1985 | Kramer |
| 4,618,261 A | 10/1986 | Flanders et al. |
| 4,663,965 A | 5/1987 | Metcalf |
| 4,689,986 A | 9/1987 | Carson et al. |
| 4,722,224 A | 2/1988 | Scheller et al. |
| 4,762,518 A | 8/1988 | Kreinick |
| 4,821,558 A | 4/1989 | Pastrone et al. |
| 4,829,448 A | 5/1989 | Balding et al. |
| 4,884,065 A | 11/1989 | Crouse et al. |
| 4,908,676 A | 3/1990 | Bedell et al. |
| 5,025,222 A | 6/1991 | Scott et al. |

(Continued)

FOREIGN PATENT DOCUMENTS

JP    2005-337937    8/2005

(Continued)

*Primary Examiner* — Hezron E Williams
*Assistant Examiner* — Alex Devito
(74) *Attorney, Agent, or Firm* — Hodgson Russ LLP

(57) ABSTRACT

A universal air bubble detector allows for use with a variety of sizes and types of tubing. The detector maintains proper alignment of a sensor emitter and receiver with different sizes of tubing. The detector may be mounted on existing equipment or may be used to monitor a tubing at any position along the tubing, and may operate in a stand alone mode or in combination with existing equipment.

11 Claims, 33 Drawing Sheets

U.S. PATENT DOCUMENTS

| | | | |
|---|---|---|---|
| 5,053,747 A | 10/1991 | Slate et al. |
| 5,074,659 A | 12/1991 | Suzuki et al. |
| 5,116,759 A | 5/1992 | Klainer et al. |
| 5,176,631 A | 1/1993 | Koenig |
| 5,191,795 A | 3/1993 | Fellingham et al. |
| 5,229,726 A | 7/1993 | Kent |
| 5,233,319 A | 8/1993 | Mizan et al. |
| 5,260,665 A | 11/1993 | Goldberg et al. |
| 5,267,221 A | 11/1993 | Miller et al. |
| 5,351,521 A | 10/1994 | Cracknell |
| 5,392,638 A | 2/1995 | Kawahara |
| 5,394,732 A | 3/1995 | Johnson et al. |
| 5,417,672 A | 5/1995 | Nita et al. |
| 5,422,495 A | 6/1995 | Cohn |
| 5,438,868 A | 8/1995 | Holden et al. |
| 5,442,495 A | 8/1995 | Saito et al. |
| 5,455,565 A | 10/1995 | Moeenziai et al. |
| 5,456,887 A | 10/1995 | Calvo |
| 5,460,178 A | 10/1995 | Hudon et al. |
| 5,475,350 A | 12/1995 | Yamada et al. |
| 5,485,743 A | 1/1996 | Taherian et al. |
| 5,514,102 A | 5/1996 | Winterer et al. |
| 5,531,680 A | 7/1996 | Dumas et al. |
| 5,534,708 A | 7/1996 | Ellinger et al. |
| 5,541,468 A | 7/1996 | Frey et al. |
| 5,672,887 A | 9/1997 | Shaw et al. |
| 5,680,111 A | 10/1997 | Danby et al. |
| D389,228 S | 1/1998 | Winterer et al. |
| 5,704,584 A | 1/1998 | Winterer et al. |
| 5,720,721 A | 2/1998 | Dumas et al. |
| 5,723,773 A | 3/1998 | Bryan |
| 5,733,061 A | 3/1998 | Child |
| 5,746,756 A | 5/1998 | Bromfield et al. |
| 5,764,356 A | 6/1998 | Iwase et al. |
| 5,789,675 A | 8/1998 | Blaine et al. |
| 5,798,050 A | 8/1998 | Gaynes et al. |
| 5,810,323 A | 9/1998 | Winterer et al. |
| 5,844,587 A | 12/1998 | Ando |
| 5,920,007 A | 7/1999 | Hirota et al. |
| 6,023,970 A | 2/2000 | Blaine |
| 6,064,577 A | 5/2000 | Moskowitz |
| 6,068,612 A | 5/2000 | Bowman et al. |
| 6,069,433 A | 5/2000 | Lazarus et al. |
| 6,110,153 A | 8/2000 | Davis et al. |
| 6,110,314 A | 8/2000 | Nix et al. |
| 6,142,008 A | 11/2000 | Cole et al. |
| 6,142,979 A | 11/2000 | McNally et al. |
| 6,192,752 B1 | 2/2001 | Blaine |
| 6,238,347 B1 | 5/2001 | Nix et al. |
| 6,328,720 B1 | 12/2001 | McNally et al. |
| D455,489 S | 4/2002 | Beck et al. |
| 6,396,583 B1 | 5/2002 | Clare |
| 6,408,679 B1 | 6/2002 | Schoder et al. |
| 6,506,035 B1 | 1/2003 | Beck et al. |
| 6,523,414 B1 | 2/2003 | Malmstrom et al. |
| 6,531,708 B1 | 3/2003 | Malmstrom et al. |
| 6,543,885 B2 | 4/2003 | Bahl |
| 6,595,950 B1 | 7/2003 | Miles et al. |
| 6,623,447 B2 | 9/2003 | Miles et al. |
| 6,636,010 B1 | 10/2003 | Malmstrom et al. |
| 6,659,976 B2 | 12/2003 | Beck et al. |
| 6,685,670 B2 | 2/2004 | Miles et al. |
| 6,709,392 B1 | 3/2004 | Salgo et al. |
| 6,749,591 B1 | 6/2004 | McNally et al. |
| 6,750,468 B2 | 6/2004 | Malmstrom et al. |
| 6,776,763 B2 | 8/2004 | Nix et al. |
| D501,924 S | 2/2005 | Cise et al. |
| 6,852,094 B2 | 2/2005 | Beck et al. |
| D503,799 S | 4/2005 | Beck |
| D503,978 S | 4/2005 | Beck |
| D504,506 S | 4/2005 | Beck et al. |
| D505,199 S | 5/2005 | Beck et al. |
| 6,902,541 B2 | 6/2005 | McNally et al. |
| 6,907,788 B2 | 6/2005 | Malmstrom et al. |
| D507,647 S | 7/2005 | Beck et al. |
| 6,923,785 B2 | 8/2005 | Miles et al. |
| 6,932,114 B2 | 8/2005 | Sparks |
| 6,949,376 B2 | 9/2005 | Kluttz |
| 6,979,311 B2 | 12/2005 | Miles et al. |
| D523,553 S | 6/2006 | Beck et al. |
| 7,070,575 B2 | 7/2006 | Beck et al. |
| 7,121,143 B2 | 10/2006 | Malmstrom et al. |
| 7,150,727 B2 | 12/2006 | Cise et al. |
| 7,152,482 B2 | 12/2006 | Ueno et al. |
| D536,783 S | 2/2007 | Cise et al. |
| 7,201,870 B2 | 4/2007 | Olsen et al. |
| 7,367,963 B2 | 5/2008 | Cise et al. |
| 2002/0169424 A1 | 11/2002 | Miles et al. |
| 2002/0192111 A1 | 12/2002 | Divino et al. |
| 2004/0220542 A1 | 11/2004 | Cise et al. |
| 2005/0004540 A1 | 1/2005 | McNally |
| 2005/0119625 A1 | 6/2005 | Miles et al. |
| 2006/0058740 A1 | 3/2006 | Cise |
| 2007/0118078 A1 | 5/2007 | McNally |
| 2007/0151346 A1 | 7/2007 | Malmstrom et al. |
| 2007/0167752 A1 | 7/2007 | Proulx et al. |
| 2008/0098798 A1 | 5/2008 | Riley |
| 2008/0103445 A1 | 5/2008 | Blaine et al. |
| 2008/0119782 A1 | 5/2008 | Steinman |
| 2008/0134750 A1 | 6/2008 | Riley |
| 2008/0208117 A1 | 8/2008 | Steinman |
| 2009/0049919 A1 | 2/2009 | Hills |
| 2009/0149801 A1 | 6/2009 | Crandall |
| 2009/0192367 A1 | 7/2009 | Braig et al. |
| 2009/0254034 A1 | 10/2009 | Beck |

FOREIGN PATENT DOCUMENTS

| | | |
|---|---|---|
| WO | WO 89/01796 | 8/1988 |
| WO | WO 98/04301 | 2/1998 |

UNIVERSAL AIR BUBBLE DETECTOR

RELATED APPLICATIONS

The present application is a continuation application of U.S. patent application Ser. No. 12/487,611, filed Jun. 18, 2009 now U.S. Pat. No. 7,818,992, which is incorporated herein by reference in its entirety, and which is a divisional of U.S. patent application Ser. No. 11/876,609, filed Oct. 22, 2007 now U.S. Pat. No. 7,726,174, and claims the benefit of U.S. Provisional Application No. 60/862,750, filed Oct. 24, 2006, and U.S. Provisional Application No. 60/949,417, filed Jul. 12, 2007, each of which are incorporated herein by reference in their entireties.

BACKGROUND OF THE INVENTION

1. Field of the Invention

The present invention relates to air bubble detectors. More specifically, the present invention relates to a universal air bubble detector which is usable with a variety of different tubing sizes and usable in a variety of different applications.

2. State of the Art

Air bubble detectors are used in many situations where it is desirable to detect the presence of an air bubble, particularly in a tube carrying a liquid. In many applications, such as the medical and health care industries, tubing is used to deliver various fluids to a person, and it is often important to detect air bubbles before they are accidentally delivered to the patient. In industry, they can be used to ensure that liquids do not have excessive amounts of air to ensure proper volume flows or reactions.

Some equipment, such as peristaltic pumps, is now available with air bubble detectors. These detectors, however, monitor air bubbles at the pump and can not check for air bubbles downstream from the pump, as may be introduced through fittings, connectors, or other equipment. It is often desirable to monitor for air bubbles downstream from the equipment and as close to the patient as possible to monitor for the introduction of air from all possible sources. There is thus a need for an air bubble detector which is capable of monitoring for air bubbles very near the point of injection of the solution into the patient, such as by attachable to a delivery tubing near the patient, or at any desired location.

Additionally, many devices are not yet available with air bubble detectors. It is often prohibitively expensive to replace equipment, or to redesign equipment to include an air bubble detector. Thus, the cost of replacing equipment or designing and manufacturing an air bubble detector may prevent the use of the same in situations where it is otherwise desirable to have the detector. There is, therefore, a need for an air bubble detector which may be attached to or used in combination with existing devices without requiring replacement or extensive modification of the device.

There are also many situations where a small number of air bubble detectors are desired, whether for a device which is produced in a limited quantity or for a project or procedure which is infrequently performed, etc. In such a situation, current air bubble detector technologies impede the use of an air bubble detector, as the detectors are typically custom manufactured for a particular application. It is appreciated that it is typically too expensive to design, create molds and tooling, and manufacture an air bubble detector where only limited quantity is desired. There is thus a need for an air bubble detector which may be used in a variety of situations, accommodating a variety of different sizes of tubing, etc.

Many available air bubble detectors function by passing a signal through the tubing and fluid and receiving the signal. The received signal is evaluated to determine if an air bubble is present. These detectors are designed to function with a particular type and size of tubing so as to achieve good signal transmission and reception. It is appreciated that if a tubing of a different diameter or type is used, the signal pathway is often interrupted, or the signal does not pass properly through the tube. Thus, a universal air bubble detector should ensure proper signal transmission and reception (signal coupling) with a variety of tubing diameters and types. Poor signal coupling typically results in errors and unreliable operation of the device.

There is thus a need for a universal air bubble detector which may be used in many different situations by allowing for mounting in a variety of locations such as at a piece of equipment or very near to a patient. Such a universal air bubble detector should accommodate a variety of different tubing diameters while maintaining good signal transmission through the tubing. Such an air bubble detector should have stand alone control circuitry and alarms or be able to connect to and communicate with associated equipment such as a delivery pump, or both.

SUMMARY OF THE INVENTION

It is an object of the present invention to provide an improved universal air bubble detector.

According to one aspect of the invention, the air bubble detector is provided with sensors which are configured for proper orientation with a variety of different sizes of tubing. It is desirable to maintain proper sensor alignment for a variety of different tubing sizes to provide good signal coupling. The sensors may be pivotably or adjustably mounted to their attachment mounts to ensure proper alignment with the tubing. The sensor mounts may also include protrusions or recesses for properly locating the tubing adjacent the sensor. Alternatively, multiple sensors may be provided and the sensor providing the best signal used for sensing air bubbles.

According to another aspect of the invention, the universal air bubble detector may be mounted in a variety of different locations, allowing flexibility in mounting and using the air bubble detector. The air bubble detector may be mounted to a pump or other piece of equipment. Alternatively, the air bubble detector may be used as a stand alone unit. The air bubble detector accepts a variety of tubing sizes and types, allowing the detector to be mounted to tubing adjacent a patient if desired.

According to another aspect of the invention, the air bubble detector may function in combination with existing equipment or may function in a stand alone unit. The detector may include wires or other communication means for communicating with existing equipment, such as with an infusion pump. The air bubble detector may also include circuitry to control operation of the detector and may control alarm means, such as an audible alarm or a light, to indicate the presence of an air bubble. As such, the detector may function as a stand alone unit.

These and other aspects of the present invention are realized in a universal air bubble detector as shown and described in the following figures and related description. It will be appreciated that the embodiments shown are exemplary of the invention and are not intended to limit the scope of the appended claims.

BRIEF DESCRIPTION OF THE DRAWINGS

Various embodiments of the present invention are shown and described in reference to the numbered drawings wherein.

It will be appreciated that the drawings are illustrative and not limiting of the scope of the invention which is defined by the appended claims. The embodiments shown accomplish various aspects and objects of the invention and it is not required that any one embodiment accomplish all aspects of objects of the invention. It is appreciated that it is not possible to clearly show each element and aspect of the invention in a single figure, and as such, multiple figures are presented to separately illustrate the various details of the invention in greater clarity. Various aspects of the drawings may be combined with aspects shown in other drawings in accordance with the principles of the present invention.

DETAILED DESCRIPTION

The invention and accompanying drawings will now be discussed in reference to the numerals provided therein so as to enable one skilled in the art to practice the present invention. The drawings and descriptions are exemplary of various aspects of the invention and are not intended to narrow the scope of the appended claims.

The present invention discloses various types of air bubble detector housings such as an enclosed conduit, adjustable clothespin type housings, adjustable channel type housings, and fixed channel type housings. Additionally, the present invention discloses various arrangements of piezoelectric sensors which present advantages such as adjustment of the threshold bubble size for detection, better detection coverage in the tubing, flow sensing, etc. It will be appreciated that the various sensor configurations, coupling elements, beam control methods, etc. which are discussed may be used in any of the detector housing shown and should be viewed as part of the various housings. For brevity, every possible sensor configuration, etc. is not shown with every possible housing configuration. Likewise, other types of sensors may be used with many of the detector configurations shown.

In discussing the drawings, similar numbers are used to discuss similar structures. For example, the number 10 is used to discuss the air bubble detector generally, such as in showing methods of using the air bubble detector according to the invention, and numbers 10A, 10B, etc. are used to show different configurations of air bubble detectors having different structures. It will be appreciated that most or all of the various air bubble detectors may be used in the various applications or methods discussed herein, and that each of the air bubble detectors may have features which are shown in conjunction with only one or a few air bubble detectors for the sake of brevity.

Figure 1A:
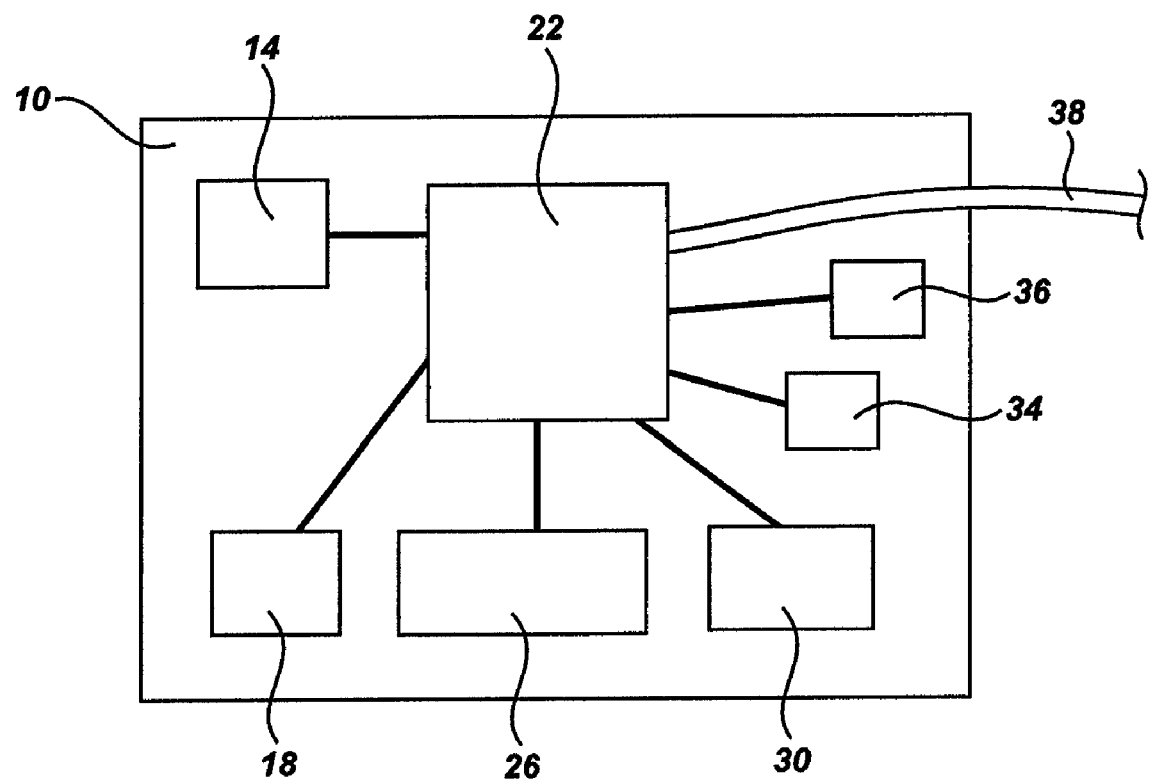
FIG. 1A shows a schematic diagram of the control circuitry of an air bubble detector of the present invention.

Turning now to FIG. 1A, a schematic diagram of the control circuitry for the air bubble detector of the present invention is shown. The air bubble detector 10 includes a sensor to detect air bubbles in a tube. The sensor may be a variety of sensors, such as an optical sensor, but according to presently preferred technologies, is typically a piezoelectric sensor, which uses ultrasound to detect air bubbles in a conduit, such as tubing. The use of optical and ultrasonic/piezoelectric sensors for bubble detection is well known in the art and is thus not discussed here in detail. The piezoelectric sensor is often a piezoelectric emitter 14 and a piezoelectric receiver 18. A controller 22 is typically used to control the operation of the air bubble detector 10, including the sensor elements 14, 18. The controller 22 will initiate the detection signals sent by the emitter 14 as well as analyze the signals received by the receiver 18 to determine if air is present. The presence of air in the tubing disrupts at least part of the signal received by the receiver 18. The controller 22 may include a preamplifier to amplify the signals received from the receiver, as well as circuitry to reduce noise.

In order to increase the accuracy of the device, the controller 22 may be used to determine the optimum operating parameters of the sensor 14, 18. Thus, when initializing the detector 10, the controller 22 may produce a frequency sweep (a varied frequency ranging from high to low or low to high) to be generated by the emitter 14. The use of frequency sweeping to ensure proper signal detection and analysis has been done for a number of years in ultrasonic sensors sold by ZEVEX, Inc. of Salt Lake City, Utah. The controller 22 can then determine which frequency was best received by the receiver 18. It is appreciated that different tubing and fluid compositions, or tubing positions may be best monitored by different frequencies. Thus, the detector 10 may select the best frequency for the particular use and operate on that selected frequency.

The detector 10 may include battery 26 to provide power to the detector, and human perceptible alarm 30 to indicate the operational status of the detector and to indicate the presence of an air bubble. The human perceptible alarm 30 may include a speaker or buzzer to provide an audible alarm if an air bubble is detected, and to provide indicator tones to indicate the correct functioning of the detector. The human perceptible alarm 30 may also have one or more lights which may be used to indicate correct operation, incorrect operation or a fault, or the detection of an air bubble.

The air bubble detector 10 may include communication devices for communicating with other equipment. The detector 10 may include a communication emitter/receiver 34, such as an IR, Bluetooth or other wireless communications module, etc. or a port 36 for receiving a communications wire. Likewise, the detector 10 may include a communications cable 38 which allows the detector to be connected to other equipment, such as a peristaltic pump, IV pump, or other device where air bubbles are a concern. The pump, or other equipment, may receive and process signals from the sensors 14, 18, may generate an alarm if an air bubble is detected, may stop if an air bubble is detected, etc. Thus, the detector 10 may transmit signals to a cooperating piece of equipment to achieve the above responses. Alternatively, the cooperating piece of equipment may control the detector 10, bypassing or working in cooperation with the controller 22, if present in the detector.

The air bubble detector 10 may thus be used in a variety of modes. The detector 10 may be used in a stand alone mode where the detector is self controlled and produces a signal or alarm if an air bubble is detected. Such may be a convenient mode of operation where the detector is used with supervision, such as during a medical procedure. It should be appreciated, however, that the air bubble detectors have a wide variety of applications outside of the medical arts.

The above description of the possibilities of control circuitry and communication devices are general for any of the various detector designs discussed below, and should be considered as part of the detectors shown in the remaining figures. In discussing the detectors shown in the remaining figures, it will be appreciated that the invention is advantageous in that it provides air bubble detectors which are capable of accommodating varying sizes and types of tubing, where existing detectors are typically designed for a single size and type of tubing.

In order to accommodate varying sizes and types of tubing, it is important that the detector provides good signal coupling to provide accurate detection of air bubbles. To achieve good signal coupling with piezoelectric sensors, the emitter and receiver should be placed on opposite sides of the tubing and should be oriented so as to be pointed at each other. Good signal coupling allows for better detection of air bubbles and for reduction in errors. The detectors described below are also advantageous as they may be placed at any desired point along the tubing, where existing detectors are typically part of a piece of equipment such as a pump. Accordingly, the detectors may be provided with mounting flanges, arms, etc., for attachment to a piece of equipment, and are typically also designed to allow mounting to a tube directly.

Figure 1B:
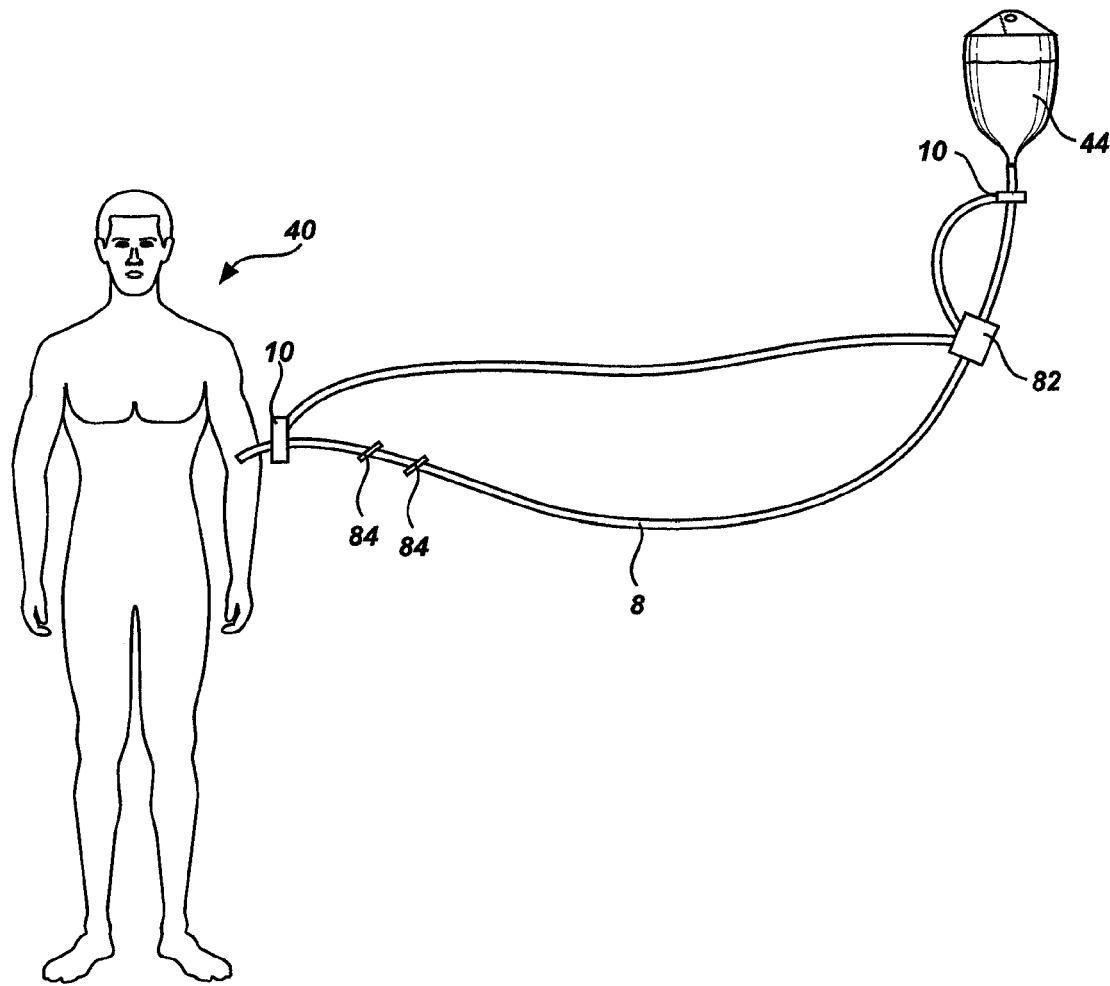
FIG. 1B shows a diagram illustrating a use of an air bubble detector of the present invention in the context of infusing a fluid into a patient.

FIG. 1B, illustrates some of the advantageous uses of the present invention. A patient 40 is being infused with fluids 44, such as blood, medication, IV fluids, etc. A similar system may be used for enteral feeding or the like. Likewise, the system may be used in non-medical uses, such as monitoring fluid flow in a laboratory, etc.

A pump 82 is used to provide the fluids to the patient at a desired rate. Existing pumps 82 are able to monitor for bubbles in the tubing contained within the pump. The pump 82 does not, however, monitor for bubbles in the tubing 8 downstream or upstream from the pump. Injection ports 84 are often provided for connection to additional fluid supplies or for manual injection via a syringe. Air bubble detectors 10 according to the present invention may be placed to monitor for air bubbles immediately prior to injection into the patient 40 (as may be introduced at the injection ports 84) or to monitor for air bubbles from the fluid reservoir 44 (or to detect a situation where the fluid is all used and air is introduced). The air bubble detectors 10 may be used to monitor tubing, drip chambers, syringes, etc. The air bubble detectors 10 may be connected to the pump 82 as shown such that the air bubble detectors automatically stop the pump or trigger another desired action.

It is thus appreciated that the air bubble detector of the present invention may be used to monitor for air bubbles at many locations. The detector may be used to monitor air bubbles present in the fluid flowing in a tube. The detector may also monitor for leaks or air introduced at fittings or connectors, or may monitor the syringes or drip chambers used to provide liquid to the system.

Figure 1C:
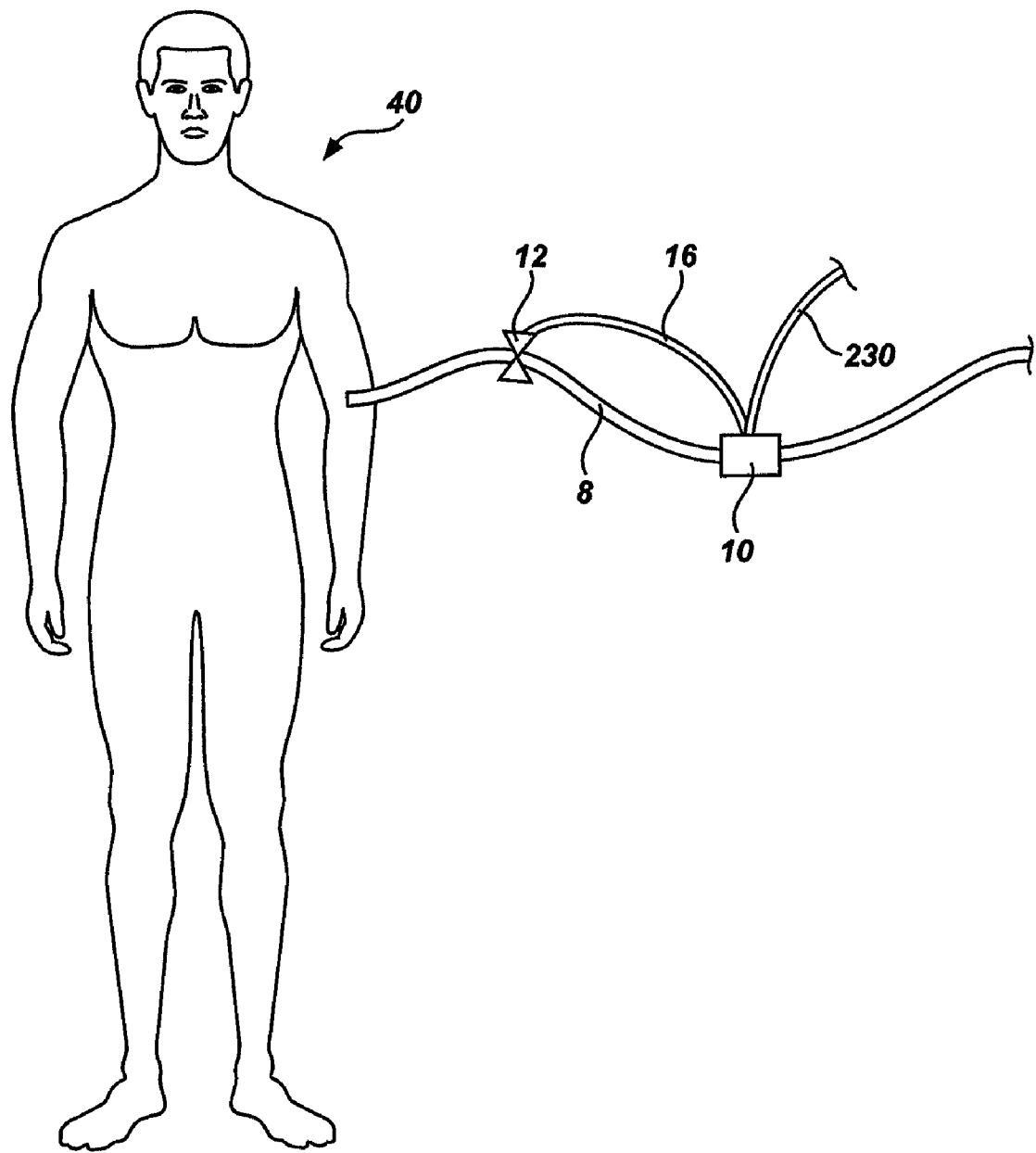
FIG. 1C shows a diagram illustrating another use of an air bubble detector of the present invention.

Turning to FIG. 1C, a diagram illustrating another use of an air bubble detector of the present invention is shown. An air bubble detector 10 may be used as a stand-alone safety device for infusing a solution into a patient 40. The air bubble detector 10 is operatively connected to a valve 12, typically via an electrical cable 16. The detector 10 is typically placed downstream of all manifolds, injection ports, etc. so as to detect any bubbles introduced through these fittings. As shown in FIG. 1B, an air bubble detector 10 may be connected to a pump to shut off or alter operation of the pump when an air bubble is detected. In some situations, the pumping system can not be stopped quickly enough to prevent an air bubble from being infused into the patient 40 along with the infusion fluid. This may be the case where high flow rates or small tubing bores are used, resulting in a short time period between fluid or a bubble passing a downstream detector 10 and entering the patient 40. Likewise, a similar set up could be used to detect air bubbles in an environment in which air bubbles are undesirable. For example a production facility which mixes precise volumes of liquids may be concerned either with excessive amounts of air which distort the mixing percentages, or the presence of air which may interfere with a desired reaction. There are numerous industrial applications for the detection of air bubbles in a stream of liquid.

FIG. 1C illustrates a system to address this situation wherein an air bubble detector 10 is connected to a valve 12 and directly operates the valve to shut off flow through the fluid transport tubing 8, such as an infusion tubing. The air bubble detector 10 would typically contain a sufficient amount of onboard circuitry to process the signals generated by air bubbles flowing through the detector and determine the size of the air bubbles, the cumulative amount of air bubbles, etc., and to transmit a signal to the valve 12 to thereby close the valve. The valve 12 would typically include a spring, solenoid, etc. capable of operating the valve to close the tubing 8.

Figure 1D:
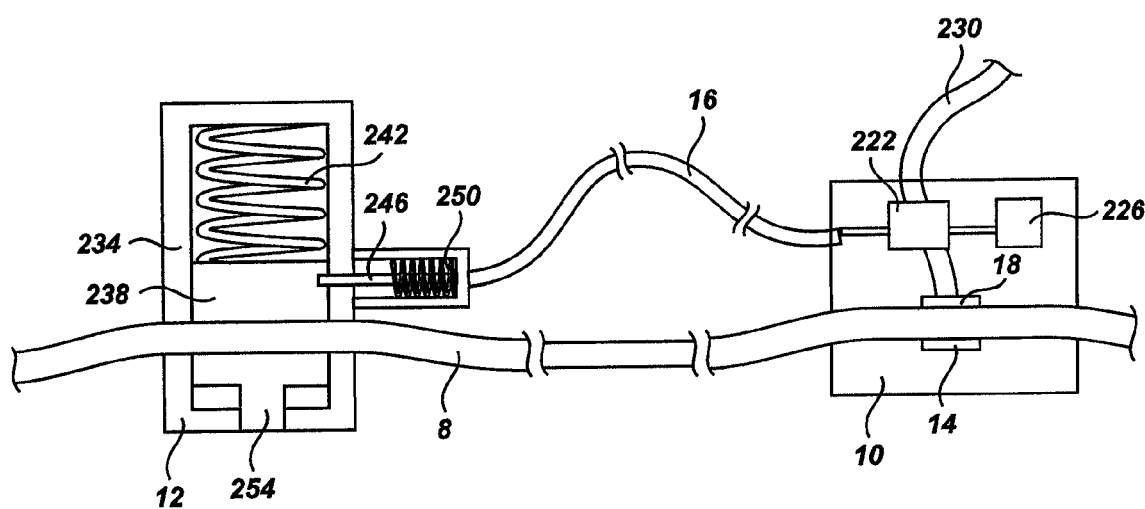
FIG. 1D shows a more detailed schematic diagram of the system of FIG. 1C.

FIG. 1D shows the detector 10 and valve 12 of FIG. 1C in greater detail. The air bubble detector 10 which is used may typically include a processor 222 which is connected to the sensor elements 14, 18 and which is capable of performing the desired processing of the sensor signal output. The processor 222 may analyze the signal output and determine when a bubble in the tubing 8 has passed through the detector 10, the size of the bubble, the total amount of bubbles, etc. The processor 222 is configured to close the valve 12 upon the occurrence of a predetermined event such as exceeding a total amount of bubble volume or detecting a bubble greater than a size limit. Upon the occurrence of such an event, the processor 222 generates a signal and transmits that signal to the valve 12 through an electrical cable 16. The detector 10 will typically have a power source 226 capable of providing power to the sensor elements 14, 18, and processor 222, and also providing necessary power to operate the valve 12. The power source 226 may be internal to the detector 10 or external. The detector 10 may also have an electrical cable 230 for connection to the pump responsible for fluid flow through the system such that the processor 222 can send a signal to stop the pump when the valve 12 is closed to prevent the buildup of excess pressure within the tubing 8.

The valve 12 may be a pinch type valve. Such a valve includes a housing 234 and a plunger 238. When the plunger 238 is in a first position within the housing 234, bores through the plunger and housing (through which the tubing 8 passes) are aligned to allow flow through the tubing. Moving the plunger 238 downwardly relative to the housing 234 to a second position misaligns the bores through the housing and plunger and pinches the tubing 8 between the housing and the plunger to prevent flow through the tubing. (The plunger need not have a bore and may be positioned on only one side of the tubing.) A spring 242 or the like may be used to bias the plunger into the second, closed position where flow through the tubing is not allowed. A trigger pin 246 may be used to hold the plunger 238 in the first position (shown) until a solenoid 250 or other suitable means pulls the trigger pin out of engagement with the plunger 238 to allow the spring 242 to move the plunger and to close the tubing 8. A push button 254 or other means may be provided to allow a person to push the valve 12 open by pushing the plunger 238 against the force of the spring 242.

The valve 12 may be operated in other ways as well, such as having a larger solenoid push directly on the plunger to close the tubing 8, etc. The configuration shown is advantageous as the solenoid 250 may require less force to pull a trigger pin 246 than the force necessary to push on the plunger and close the tubing 8, reducing the power necessary to operate the valve 12. Additionally, the configuration shown does not require continued input from the detector 10 to keep the valve 12 closed after the initial closing of the valve.

The detector 10 and valve 12 may be provided with the necessary tubing 8 and connectors for attachment to a patient (or some other end location of the fluid stream) and to the rest of the system, i.e. to the pump, manifold, syringe ports, etc. Thus, a system may be provided which includes the detector 10, valve 12, and tube 8 in an assembled unit. The detector 10 or tube 8 may include fittings such as luer fittings for connection to the patient and to the fluid infusion system. Thus, the detector 10 may have a luer lock fitting on the inlet side for connection to the upstream infusion tubing, tubing 8 extending from the outlet side of the detector and terminating in a luer lock connector or the like for connection to a patient 40, and the valve 12 disposed along the tubing and connected electrically to the detector. The detector 10 may also include a wire for connection to the pump or infusion system. It will be appreciated that it is desirable to have a reasonable length of tubing 8, such as a few feet, between the detector 10 and the valve 12 to provide a slight time delay between the passing of a bubble through the detector and the passing of the same bubble through the valve. Such time delay will allow the valve to close before the bubble reaches the valve. It may be equally effective to stop the fluid flow after the bubble has passed the valve 12 but before it has entered the patient 40.

Figure 2A:
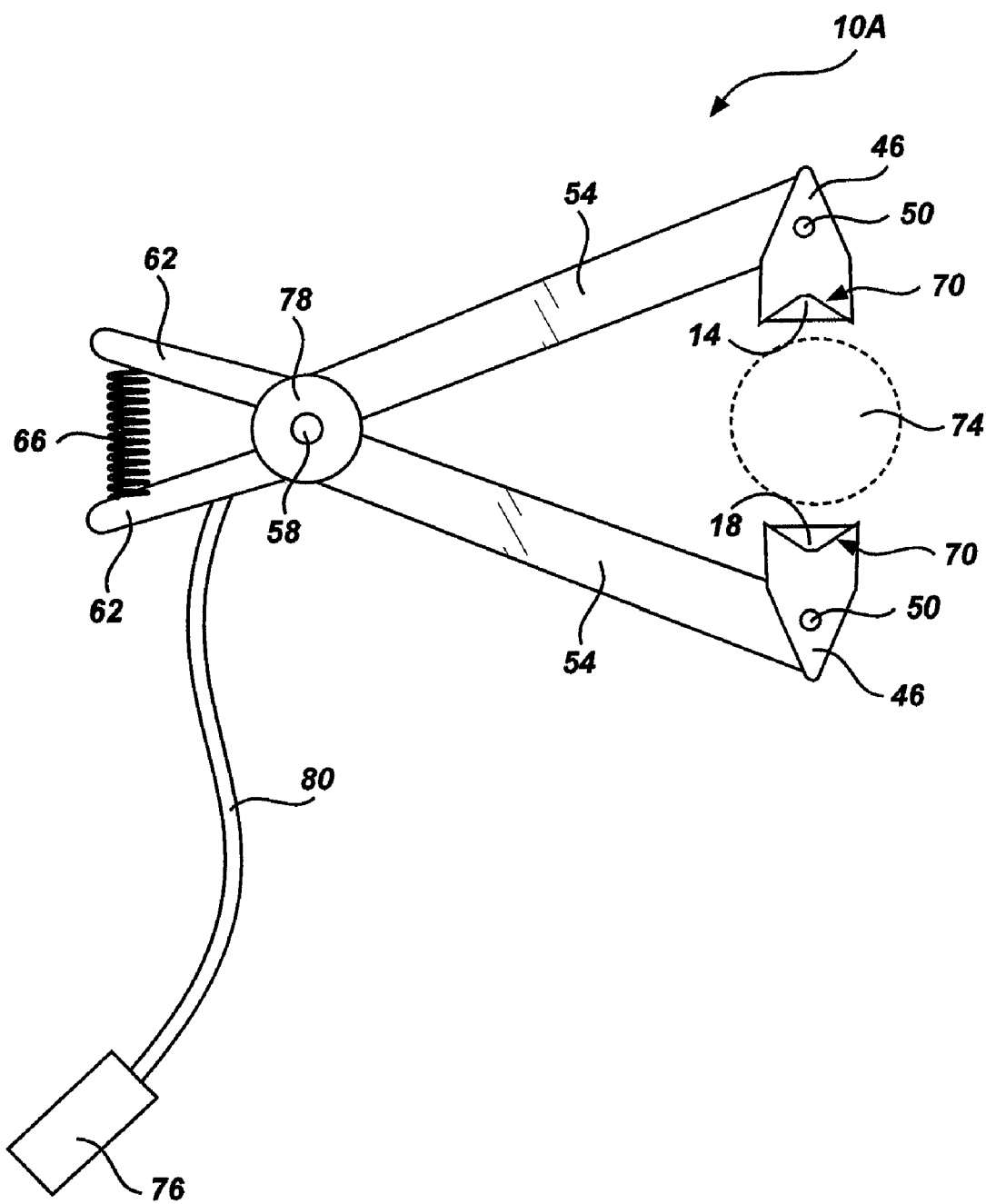
FIG. 2A shows an end view of an air bubble detector of the present invention.

Turning now to FIG. 2A, an end view of an air bubble detector 10A of the present invention is shown. The air bubble detector 10A includes a piezoelectric or ultrasonic emitter 14 and receiver 18 which are mounted in sensor mounts 46. The sensor mounts 46 are attached via pivots 50 to arms 54. The arms 54 are attached to each other at a pivot 58, and may include extensions 62 to facilitate opening of the detector to increase the distance between the mounts 46 in a manner similar to how a clothespin operates. A spring 66 or other biasing element is typically used to bias the detector 10A into a closed position by moving the mounts 46 closer together. It will be appreciated that the spring 66 may be formed on either side of the pivot 58 or formed integrally with the pivot.

The mounts 46 are mounted via a pivot 50 to allow the mounts to pivot and thereby be placed in a linear arrangement when different diameters of tubing are placed therebetween. It is appreciated that if the mounts 46 did not pivot, the mounts would move out of alignment with each other as the detector was opened or closed (via pivot 58). The mounts 46 may also be attached to each other or to pivot 58 via rods, levers, gears, etc. such that the attachment mechanically pivots the mounts 46 as the device is opened or closed to thereby align the mounts.

The mounts 46 may include a centering member, such as notch 70 formed therein which aids in centering the monitored conduit 74, such as tubing, syringe, drip chamber, etc., over the sensors 14, 18. Hereafter the conduit is often referred to simply as tubing, as such is a common use. These notches 70 may be used to increase the accuracy or reliability of the detector 10A. The sensors 14, 18 may be formed with a variety of shapes for the surface which contacts the tubing 74. The contacting surface may typically be flat or slightly convex such that the tubing 74 conforms slightly to the sensor, increasing the signal quality. Thus, the biasing spring 66 may be selected such that it applies sufficient pressure on the tubing 74 to cause the tubing to conform to the sensor somewhat.

The pivot 58 may include a device to detect how far open the detector 10A is, such as a potentiometer 78 or other sensing means. The resistance across a potentiometer could be easily measured by the controller 22 (FIG. 1). Such information could be used to determine optimum operating conditions. Additionally, the potentiometer 78 could be monitored during use of the detector 10A to determine if the tubing 74 was properly loaded. If the tubing was suddenly removed from the detector 10A, the detector would close and the resistance of the potentiometer would change. The potentiometer 78 or other sensing means may also be used to detect changes in pressure in the tube. Changes in pressure in the tube will expand the tube somewhat, which will cause expansion of the air bubble detector and change the measured value of the position sensitive device, such as potentiometer 78. Other sensors such as hall sensors, optical sensors, strain sensors, etc could be used in place of the potentiometer 78.

For all of the various air bubble detectors described herein, the controller 22, etc. as detailed in FIG. 1 may be carried on the detector, or may be in a module 76 remote from the detector and disposed in communication with the sensors 14, 18 via a communications cable 80, allowing greater flexibility in using the detector 10. Additionally, the controller and associated circuitry could be contained within a pump or other device and the air bubble detector 10 have a cable which can be connected to the device, allowing the detector to be placed remotely from the device, such as downstream or upstream of the device.

Figure 2B:
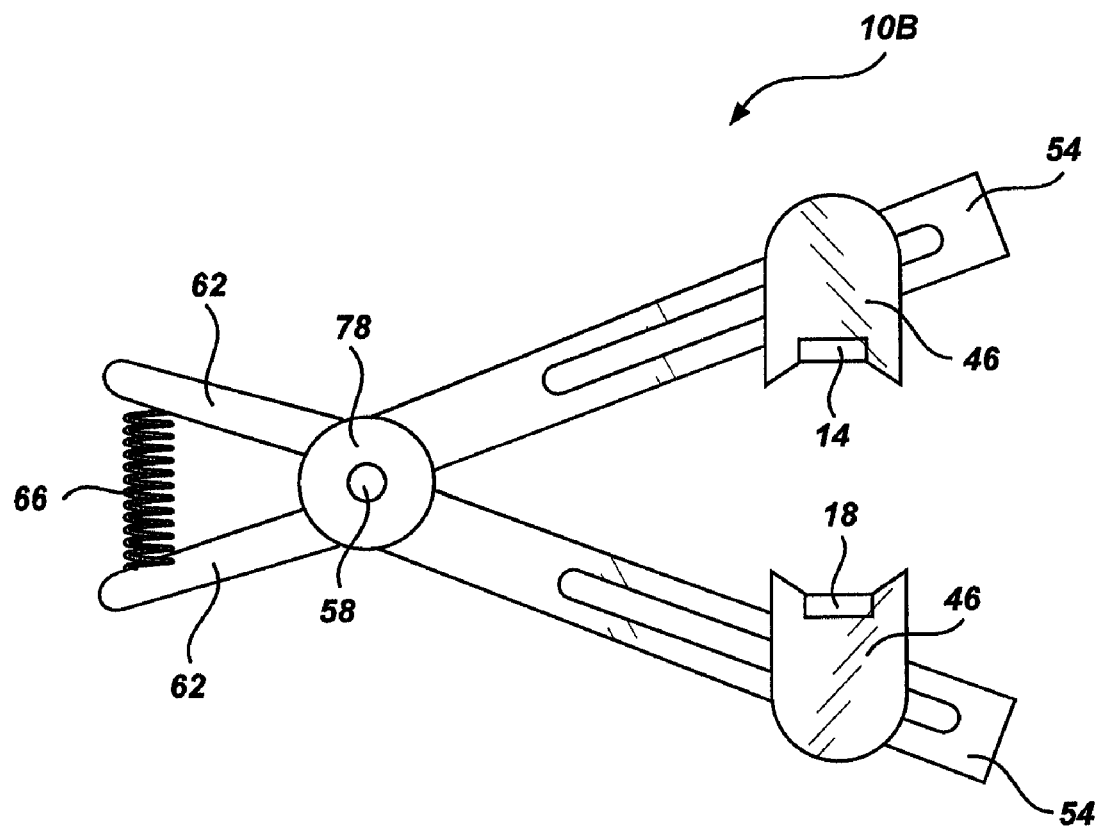
FIG. 2B shows an end view of an air bubble detector of the present invention.

FIG. 2B shows a side view of another clothespin type air bubble detector 10B similar to that shown in FIG. 2A. Parts or structures which are similar and which have similar function as those discussed above are numbered accordingly. The sensors 14, 18 are attached to mounts 46 which are slidably attached to the arms 54. The mounts 46 may be slid inwardly and outwardly along the arms 54 so as to place a lesser or greater distance between the sensors 14, 18 which maintaining the same angular relationship between the mounts.

Thus, the detector 10B may be designed to hold a conduit between the sensors 14, 18 and maintain proper alignment between the sensors 14, 18 when the arms are disposed at a selected angle relative to each other. For example, the sensors 14, 18 and mounts 46 may be positioned on the arms 54 at a 20 degree angle, such that they are aligned with each other and in the orientation shown when the arms 54 are disposed at an angle of 40 degrees relative to each other. Sliding the mounts 46 along the arms 54 will increase or decrease the distance between the sensors 14, 18 and accommodate conduits of varying size while maintaining the desired sensor alignment.

Figure 2C:
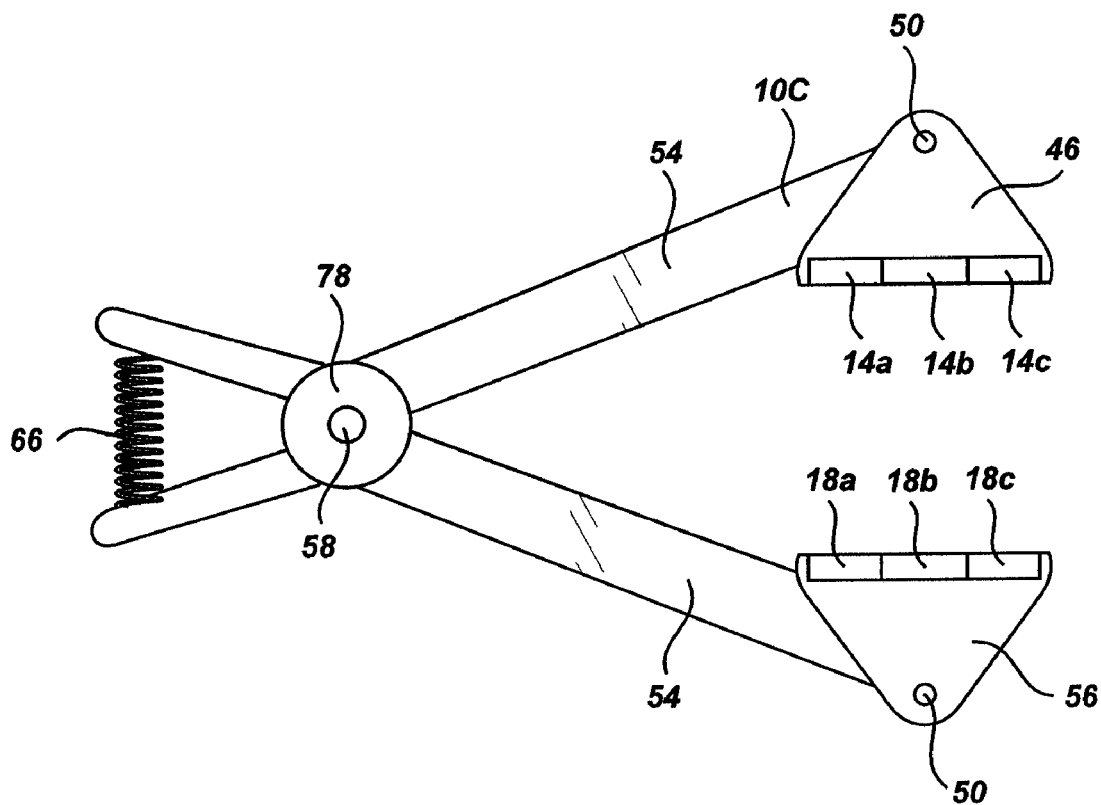
FIG. 2C shows an end view of an air bubble detector of the present invention.

Turning now to FIG. 2C, a side view of another clothespin type detector 10C of the present invention is shown. The detector 10C has sensor arrays 14a-14c, 18a-18c attached to mounts 46 The mounts 46 may be pivotably attached to the arms 54 via a pivot 50. Using multiple sensors 14a-14c, 18a-18c may aid in obtaining good signal coupling and reception.

It is desirable to send ultrasonic energy only through the fluid or air filled portion of the tubing, and not around the perimeter of the tubing, such as through liquid or the like on the outside of the tubing. This avoids the coupling, or transmitting, of energy from transmitter to receiver around the desired sensing area inside the conduit, and aids in maintaining a high signal to noise ratio. Coupling paths whereby the ultrasonic signals may be transmitted while avoiding the lumen of the conduit include the air bubble detector housing, parent system that the ABD is mounted on, tubing wall, etc. Often more importantly, condensation or spillage onto the sensor or conduit could conduct energy from transmitter to receiver around the conduit and not through the conduit lumen, and this may cause fluid to be sensed when air is present. By using an array of sensors 14a-14c, 18a-18c, the detector 10C may determine which sensors provide the optimal signal path and will best detect air bubbles. Alternatively, the conduit size, as indicated by the potentiometer 78, could be used to determine the optimum sensor elements used.

Figure 2D:
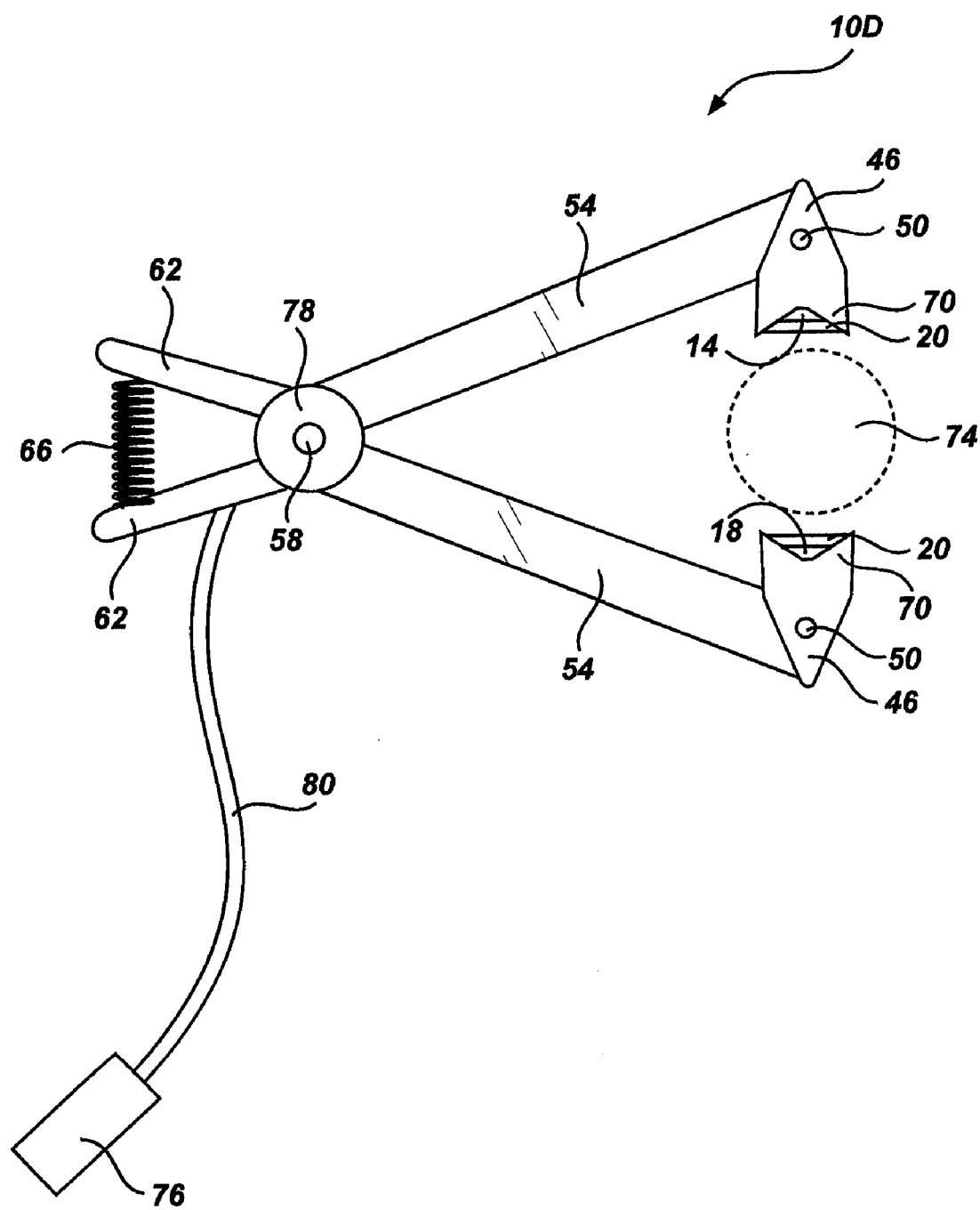
FIG. 2D shows an end view of an air bubble detector of the present invention.

FIG. 2D shows a side view of a clothespin type detector 10D similar to that of FIG. 2A and labeled accordingly. The detector 10D includes soft coupling elements 20 placed over the piezoelectric emitter 14 and receiver 18. The coupling elements 20 are made from a compliant material which conforms to a rigid surface and which transmits the ultrasonic frequencies such as urethane. Typically, it is desirable to use a compliant coupling element 20 with a rigid tubing or conduit, and a rigid sensor surface with a compliant tubing to achieve good acoustic coupling. The coupling elements 20 aid in transmitting the ultrasonic signals into a rigid tubing, drip chamber, syringe, metal tubing, etc. It is appreciated that most or all of the embodiments shown herein may incorporate such a soft coupling element, but such an element is not shown in every case for clarity.

Figure 3:
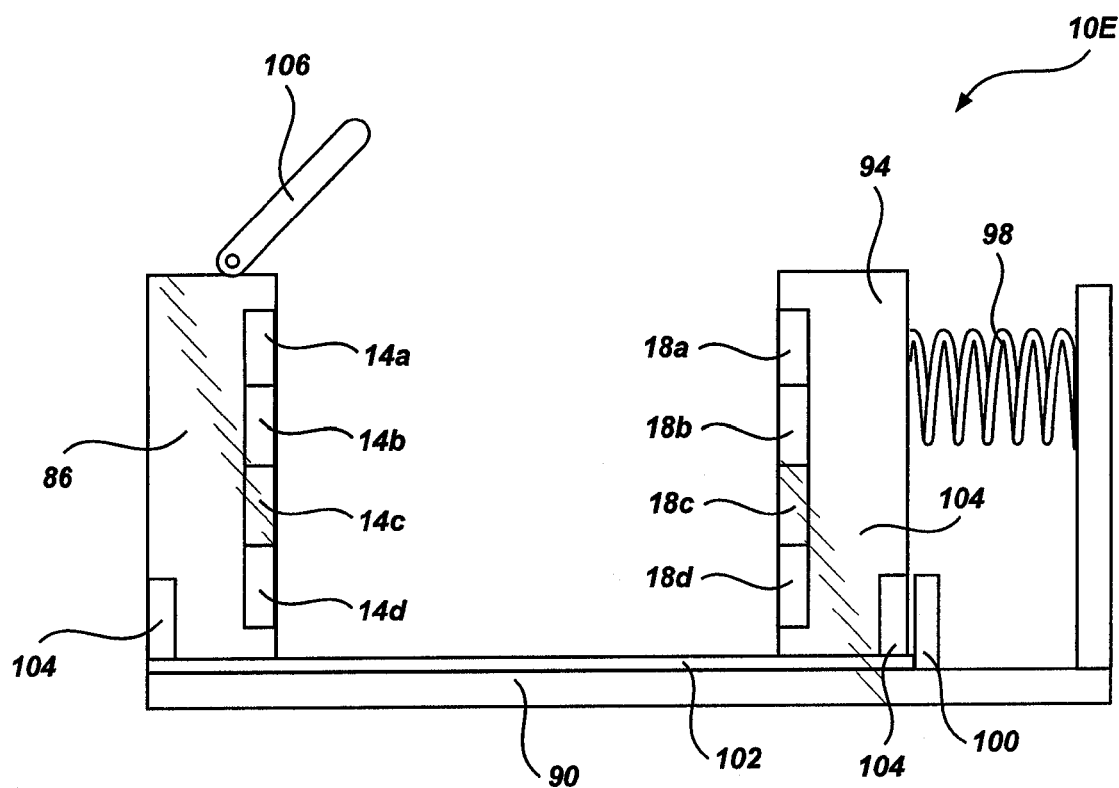
FIG. 3 shows an end view of an air bubble detector of the present invention.

Turning now to FIG. 3, an end view of another detector 10E of the present invention is shown. The detector 10E has a plurality of piezoelectric emitters 14a-14d mounted to a mount 86 (such as an arm or flange extending upwardly from the detector base). The mount 86 is connected to a base 90. A second mount 94 is slidably mounted to the base 90 and has a plurality of piezoelectric receivers 18a-18d mounted thereto. The second mount 94 may be slid back and forth to accommodate different sizes of tubing. The second mount 94 may be biased closed with a spring 98 or other biasing element, or may be locked in position by the user, such as by the use of a locking member 100. The locking member 100 may be a movable cam or lever which holds the second mount 94 in place. Additionally, a slidable attachment 104 may be made between the mounts 86, 94 and the base 90 to adjust the height of the mounts if needed.

The base 90 may include a linear resistor 102 which is used to detect the position of the second mount 94 along the base 90. The linear resistor 102 may be a resistive strip with a first contact point adjacent the mount 86 and a second contact point mounted on the base of the second mount 94 such that movement of the second mount 94 moves the second contact point and varies the resistance across the resistor.

During setup, the controller 22 may operate each pair of emitter/receiver (such as 14a, 18a) to determine which pair of emitter 14 and receiver 18 provides the best signal. The controller may also use information from the variable resistor 102 to aid in selecting an emitter 14 and receiver 18, or may make the selection based solely on the variable resistor. Additionally, the variable resistor 102 may be used as discussed above to determine if the tubing has been removed from the sensor 10E. As alternatives to a variable resistor 102, a variable capacitor, optical sensors, etc. may be used to determine the position of the detector 10E. Additionally, optical sensors, switches, etc. may be used to determine the presence of tubing in this and the other detectors 10 shown. It may be desirable that the detector 10E also include an arm, latch, or other structure 106 to keep the tubing against the base 90 to prevent the tubing from sliding out of the detector or sliding to be adjacent a different sensor pair 14, 18.

Figure 4:
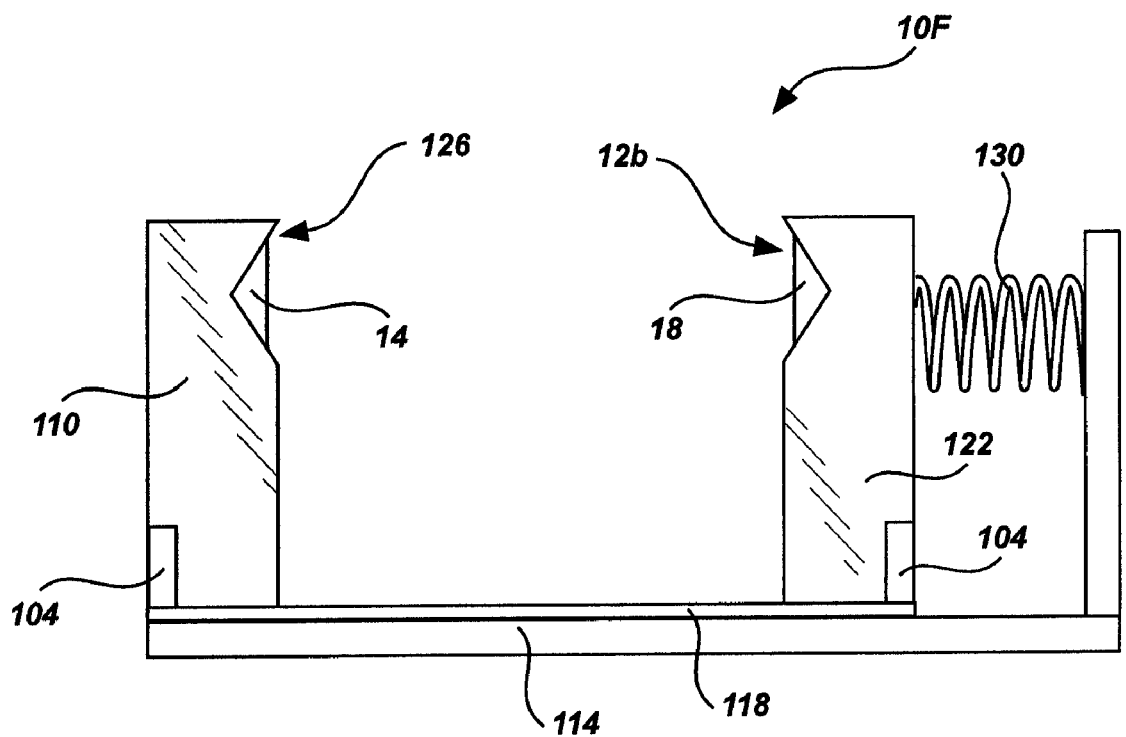
FIG. 4 shows an end view of an air bubble detector of the present invention.

Turning now to FIG. 4, an end view of another detector 10F is shown. The detector 10F is similar to that of FIG. 3, having a first mount 110, base 114, variable resistor 118, and second mount 122 slidable along the base 114, and may include a height adjustment mechanism 104 (such as a slide, etc.) which allows the relative height of the sensors 14, 18 to be adjusted. The mounts 110, 122 include a piezoelectric emitter 14 and receiver 18, and include tube alignment members such as notches 126 similar to those of FIG. 2. The notches 126 align the tubing with the sensors 14, 18. A spring 130 may be used to bias the second mount 122 against the first mount 110 and hold the tubing in place. As discussed before, the spring 130 may provide sufficient force to conform the tubing somewhat to the sensors 14, 18 to improve the transmission of signals. The variable resistor 118 functions in a manner similar to those of FIGS. 2 and 3.

Figure 5:
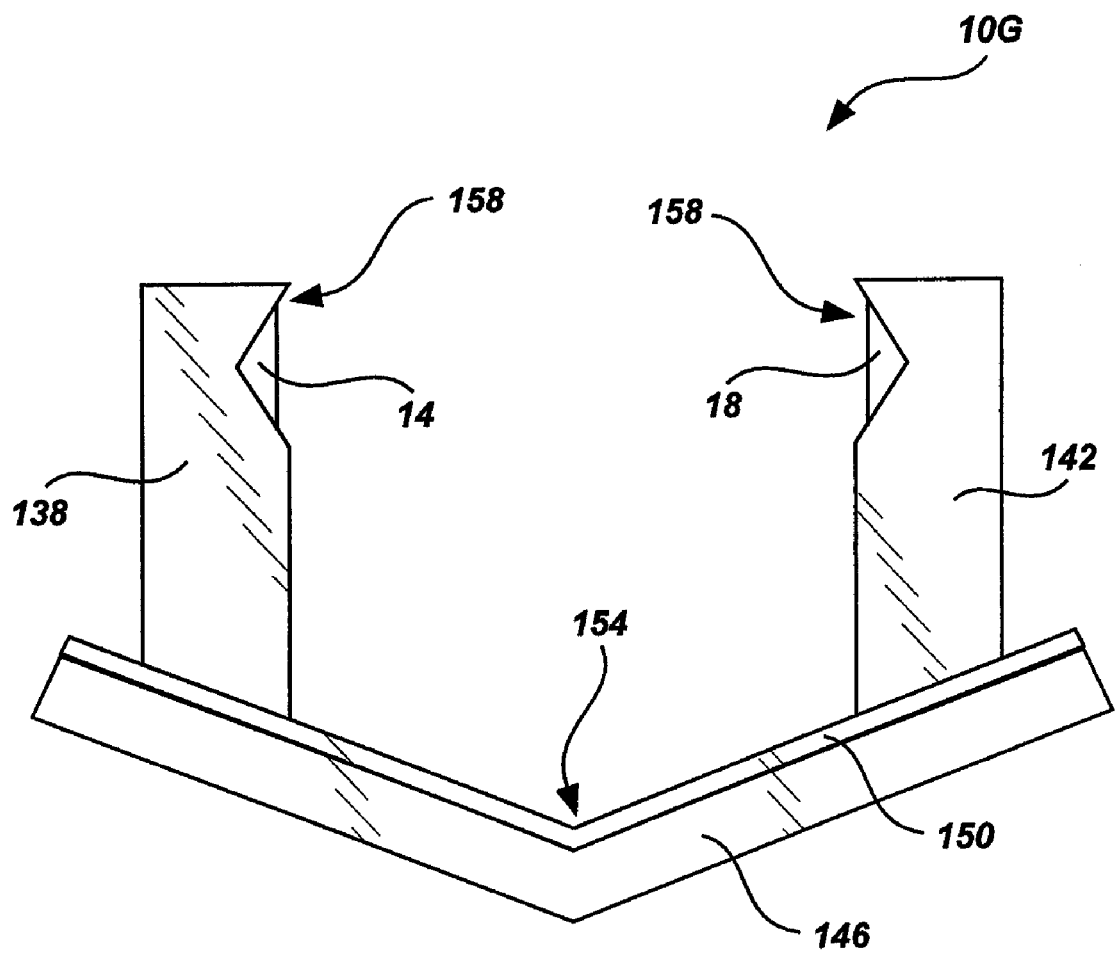
FIG. 5 shows an end view of an air bubble detector of the present invention.

Turning now to FIG. 5, an end view of another detector 10G is shown. The detector 10G is similar to those of FIGS. 3 and 4. A first mount 138 and second mount 142 are both slidably mounted to a base 146, which may include a variable resistor 150, functioning as has been discussed above. The base 146 is angled (i.e. V-shaped or U-shaped) such that the sensors 14, 18 can change height relative to the bottom trough, indicated generally at 154, of the base 146. The change of height raises the sensors 14, 18 as they are moved apart to better accommodate varying tubing sizes. The angle(s) at which the base 146 is bent may be chosen such that a larger or smaller tubing will rest against the base 146 when properly loaded. The mounts 138, 142 may also, or alternately, include notches 158 to secure and align the tubing.

Figure 6:
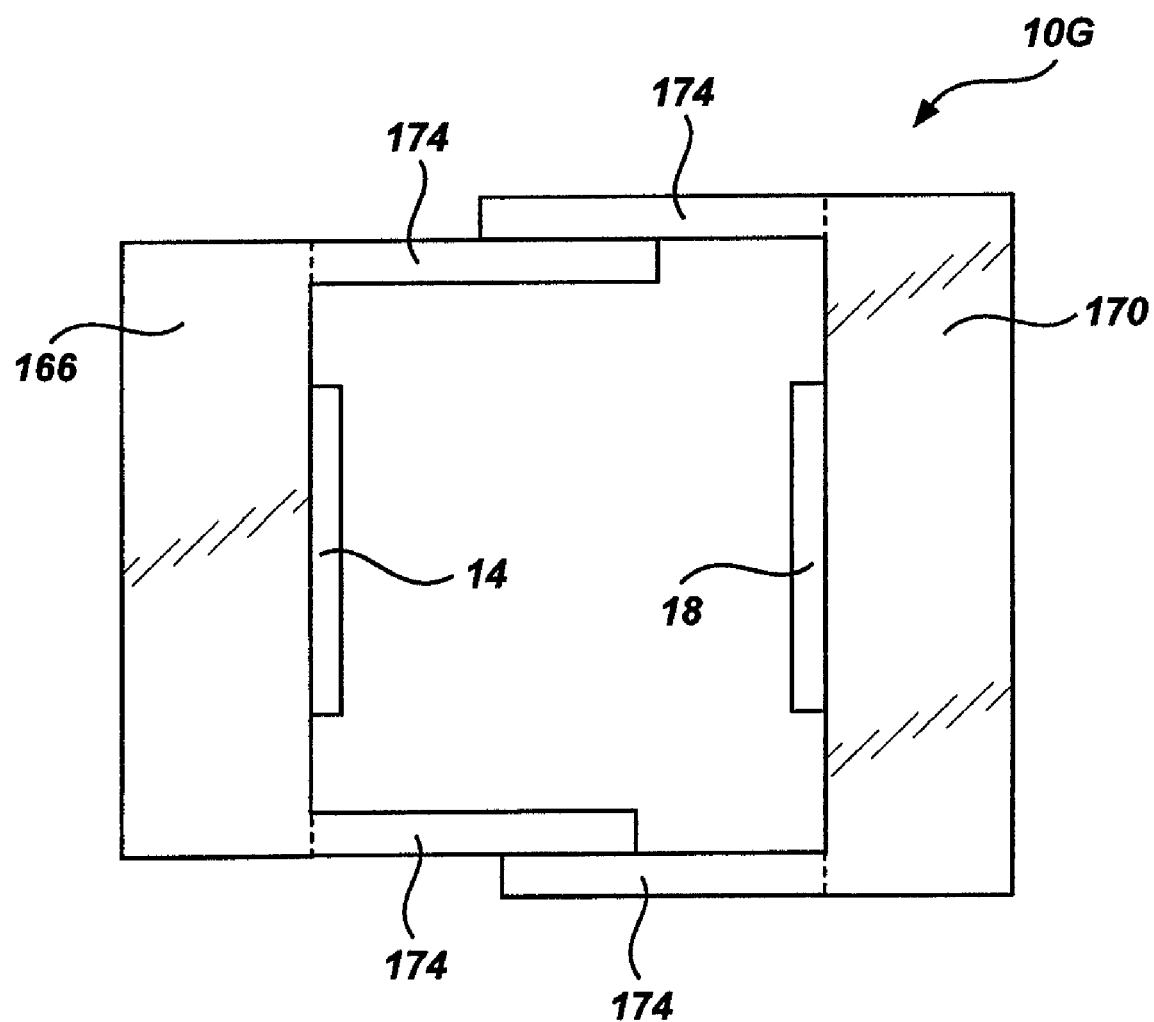
FIG. 6 shows a top view of a sensor mount of the present invention.

Turning now to FIG. 6, a top view of the detector 10G of FIG. 5 is shown, more clearly illustrating the alignment mechanism of FIGS. 2, 4, and 5. The mounts 166, 170 are shown with the sensors 14, 18 mounted thereto. The alignment mechanism, such as notches 174 may be formed as extensions from the mounts 166, 170, having the V-shaped (or other shape) cutout formed in them as shown in FIGS. 2, 4, and 5. The notches 174 may be positioned somewhat away from the sensors 14, 18 so as to not interfere with the conformation of the tubing to the sensor, and may also be positioned so as to not interfere with each other, or even overlap each other when closed, capturing the tubing within the cutout to prevent removal of the tubing. It will be appreciated that the alignment mechanism, such as notches 174, may be disposed on only one of the mounts 166, 170 if desired.

Figure 7:
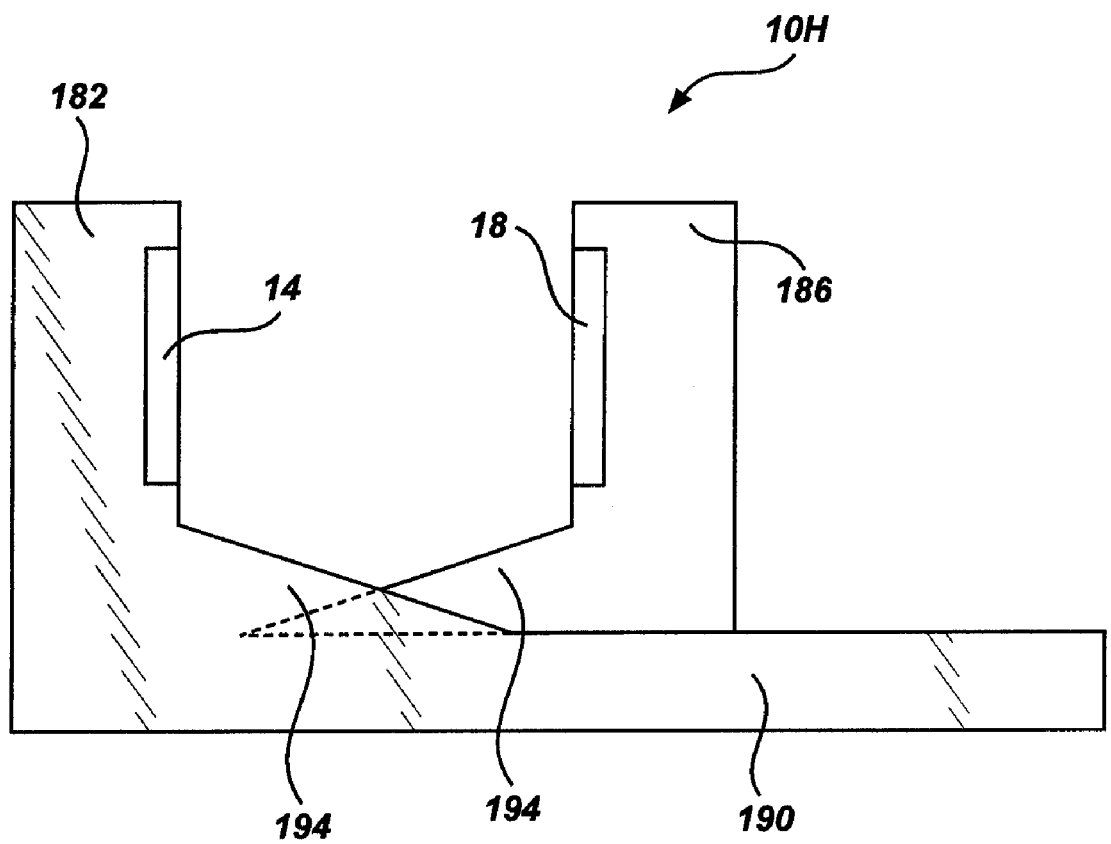
FIG. 7 shows an end view of an air bubble detector of the present invention.

Turning now to FIG. 7, an end view of another detector 10H is shown. The detector 10H includes a first mount 182 and a second mount 186 having sensors 14, 18 attached thereto. The first mount 182 is attached to a base 190, and the second mount 186 is slidably attached to the base, such as by being mounted on rails or in a channel. One or both of the mounts 182, 186 may have an incline 194 attached thereto, such that the second incline or mount is slidable past the first incline as shown to effectively increase the height of the surface between the sensors 14, 18 upon which the conduit will rest. The inclines 194 are formed with an angle or a curved surface to maintain conduits of varying sizes centered on the sensors 14, 18 when the mounts 182, 186 are placed at the appropriate distance from each other for the particular conduit. The detector 10H may have the other structures such as a variable resistor, retaining arms, locking levers, multiple sensors, etc. as have been previously discussed. It is appreciated that, for brevity and clarity, not all structures are discussed with respect to each detector embodiment. It is understood that each embodiment may include such features or structures to the extent that the features do not contradict with those specifically discussed with that embodiment.

The detector 10H may be locked in position in a variety of ways. A lever or locking cam may be provided to lock the mount 186 into a position relative to the base 190 and allow adjustment. Additionally, the mount 186 may be permanently fixed relative to the base as a final step in manufacturing or when in use. The mount 186 may be permanently attached to the base 190 in a variety of ways, such as by using glue to fix the position, melting the material (typically plastic) to fuse the mount to the base, using a solvent to weld the mount to the base, etc. The detector 10H is thus advantageous as a sensor produced for custom applications as it may be manufactured in large quantities with the sliding mount 186, and then easily customized for a particular application by fixing the location of the mount 186 to fit a particular tube or conduit. It is appreciated that these techniques for fixing the distance between the sensors 14, 18 could be used with any of the detector embodiments discussed herein.

Figure 8:
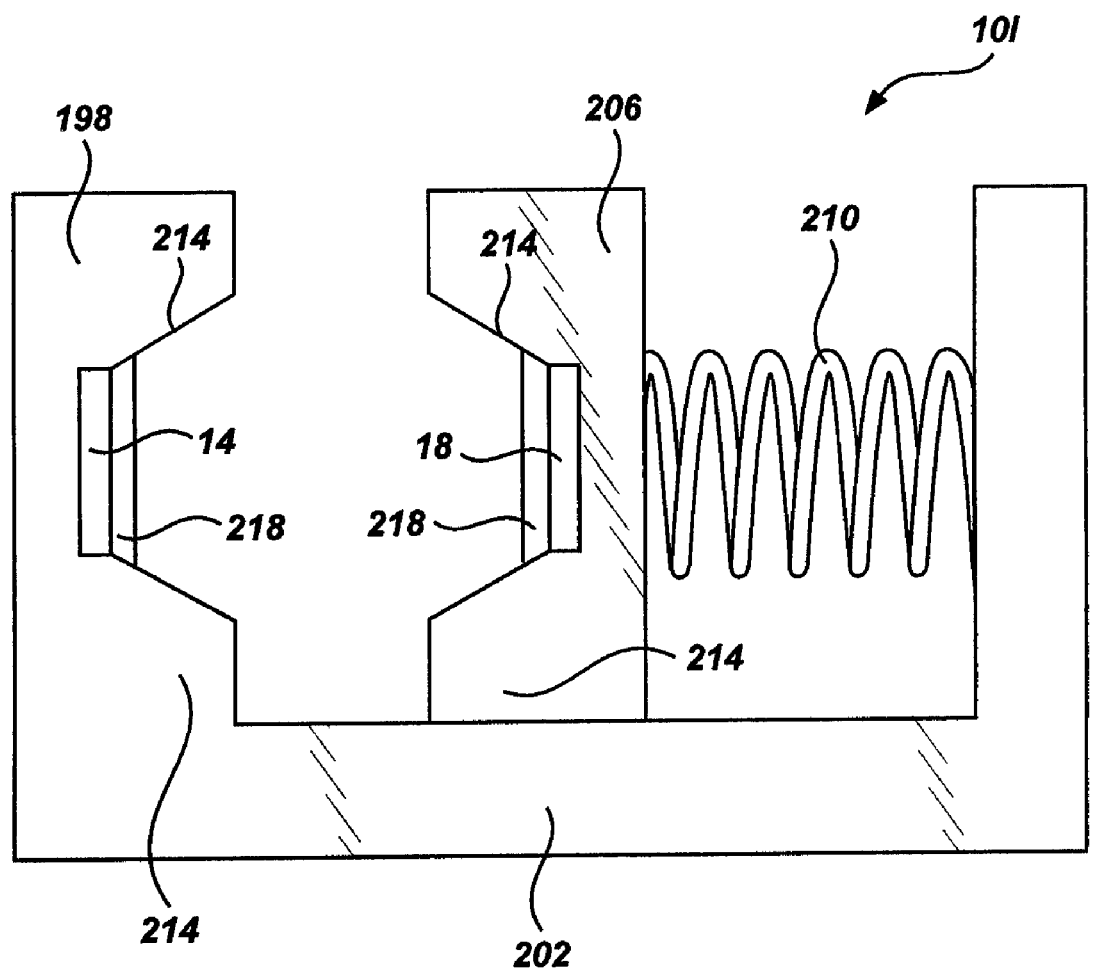
FIG. 8 shows an end view of another air bubble detector of the present invention.

Turning now to FIG. 8, an end view of another detector of the present invention is shown. The detector 10I includes a first mount 198 with sensor 14 which is fixed to the base 202 and a second mount 206 with sensor 18 which is slidable relative to the base. A spring 210 or other biasing structure (elastic, etc.) is used to bias the mounts 298, 206 towards each other. The mounts 198, 206 are formed with alignment structures 214 disposed on either side of the sensor 14, 18, which may be formed as angled surfaces. The alignment structures 214 essentially form notches which aid in locating the conduit between the sensors 14, 18. A compliant material 218, such as a silicone, may be disposed over the sensors 14, 18 to improve the coupling with a rigid conduit, such as a syringe, a drip chamber of a rigid conduit for carrying liquids in a production facility of laboratory. It is appreciated that any of the above detector embodiments may have such a compliant material attached to the sensors. Alternatively, a compliant insert may be provided to aid in signal coupling with a rigid conduit.

Figure 9:
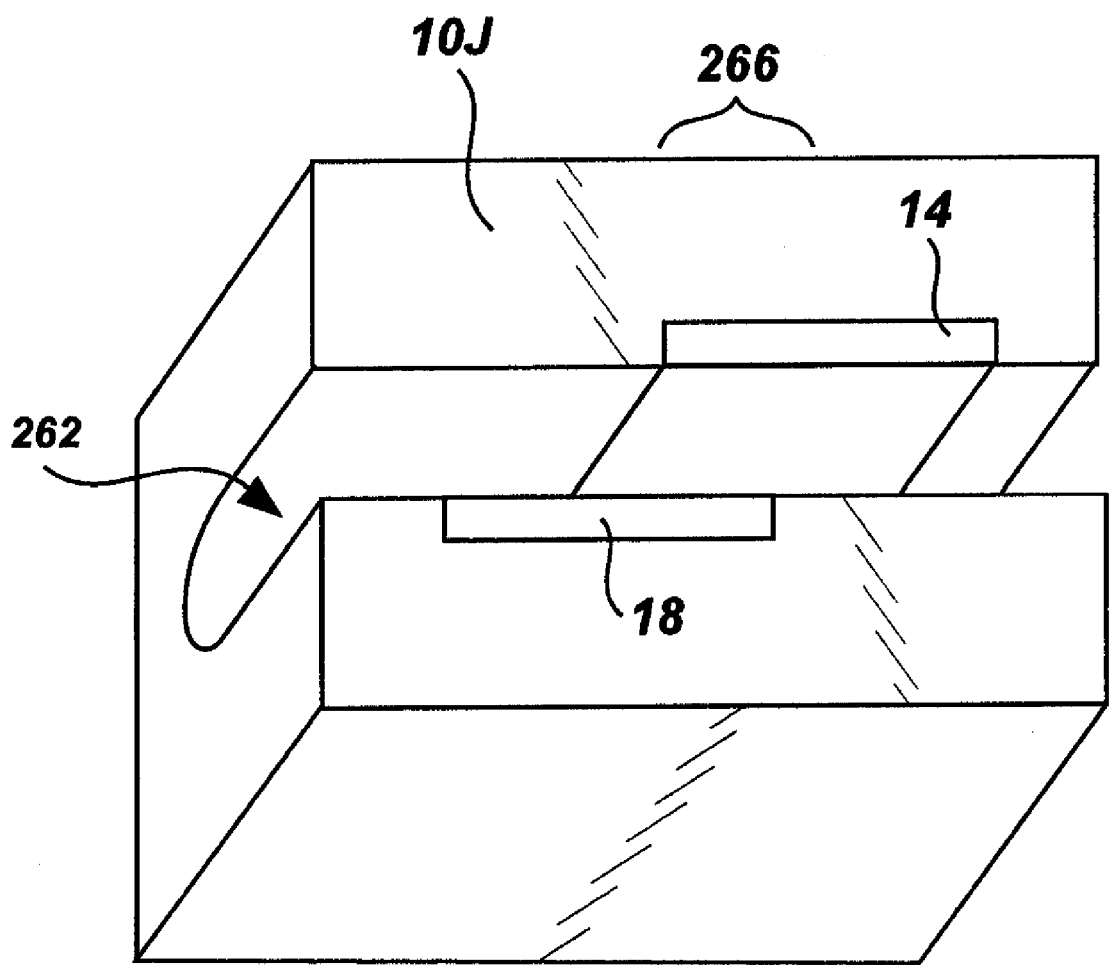
FIG. 9 shows a perspective view of a sensor configuration for the detectors of the present invention.

Turning now to FIG. 9, a perspective view of another air bubble detector 10J is shown. The detector 10J includes a piezoelectric sensor comprising an emitter 14 and receiver 18. The emitter 14 and receiver 18 are placed on mounts which define opposite sides of a channel 262 which receives a tube therein such that the emitter 14 and receiver 18 are disposed on opposite sides of the tube. The emitter 14 and receiver 18 have been placed in the detector 10J such that the emitter and receiver only partially overlap each other. In constructing such a detector 10J, the emitter 14 and receiver 18 may be moved along the channel to vary the overlap and then bonded or otherwise fixed in place along the channel 262.

Reducing the overlap 266 will make the detector able to detect smaller bubbles as well as larger bubbles, but will reduce the signal strength (which is roughly proportional to the overlapping area) and require greater amplification of the signal, which may result in more noise. Increasing the overlap 266 will reduce the ability of the detector to detect smaller bubbles (raising the threshold bubble size for detection) but will increase the signal strength from the sensor. It is appreciated that the emitter 14 and receiver 18 need not be placed on the surface of the channel 262, but may be adhered to the detector from the back side of the channel or be placed into a pocket formed therein so long as good acoustic coupling is achieved and so long as the materials used transmit ultrasonic frequencies. It will be appreciated that the varied overlap 266 between the emitter 14 and receiver 18 as shown in FIG. 9 may be used with most, if not all, of the detectors shown herein. As such, the varied overlap should be considered as part of those detectors.

Figure 10:
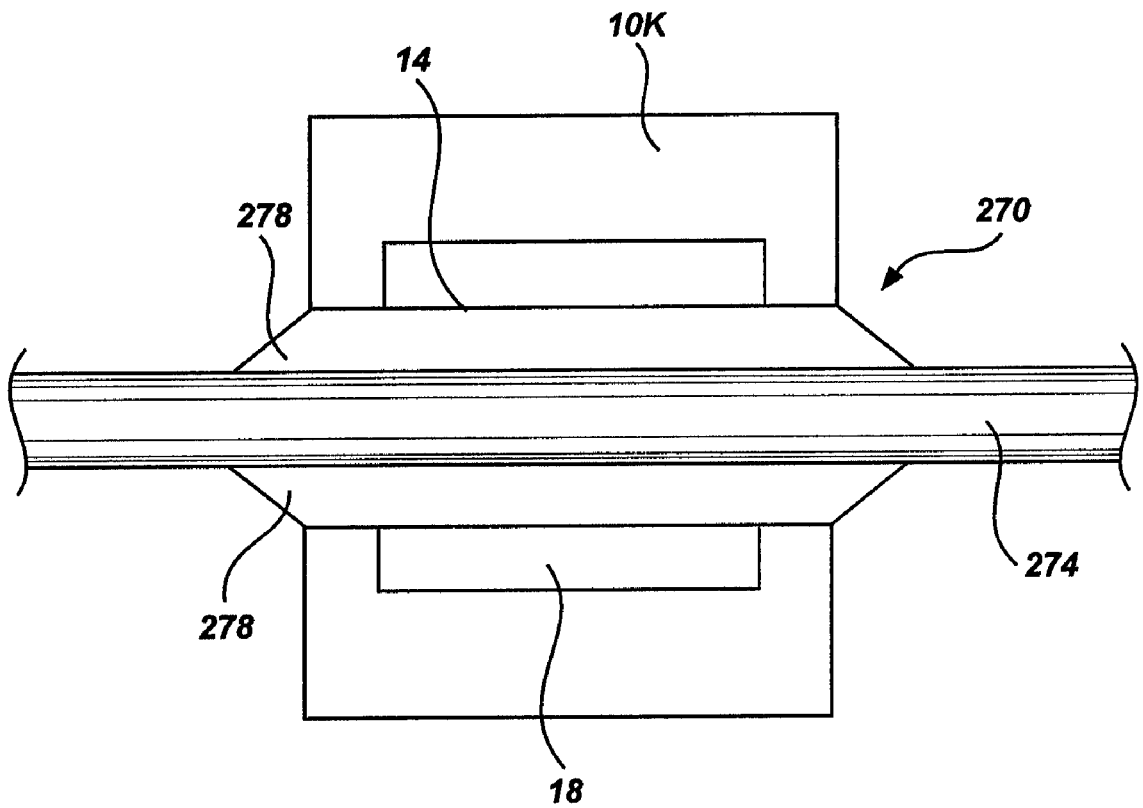
FIG. 10 shows a top view of a sensor configuration for the detectors of the present invention with a fluid transport tube disposed therein.

Turning to FIG. 10, a top view of another sensor configuration for an air bubble detector 10K is shown. The air bubble detector 10K includes an emitter 14 and receiver 18 mounted on opposite sides of a channel 270. In order to achieve good acoustic coupling with a rigid tube 274, a compliant coupling sleeve 278 has been formed or mounted on the rigid tube. It has been discussed above how a detector 10 may have a compliant surface placed over the emitter/receiver surface to achieve good coupling to a rigid tube or object. In certain situations it is advantageous to form the compliant coupling element on the rigid tube, such as where the rigid tube is part of a pump cassette or the like. The compliant sleeve 278 will be replaced when the cassette is replaced, minimizing the effects of wear and tear on the sleeve. To achieve good acoustic coupling, it is typically desirable that only one of the tube and the detector surface be compliant and the other be rigid. It will be appreciated that the compliant sleeve 278 may used with any of the various detector designs shown herein and should be considered as part of these designs. The sleeve 278 may be formed from a material such as urethane, thermoplastic elastomer, silicone, etc.

Figure 11:
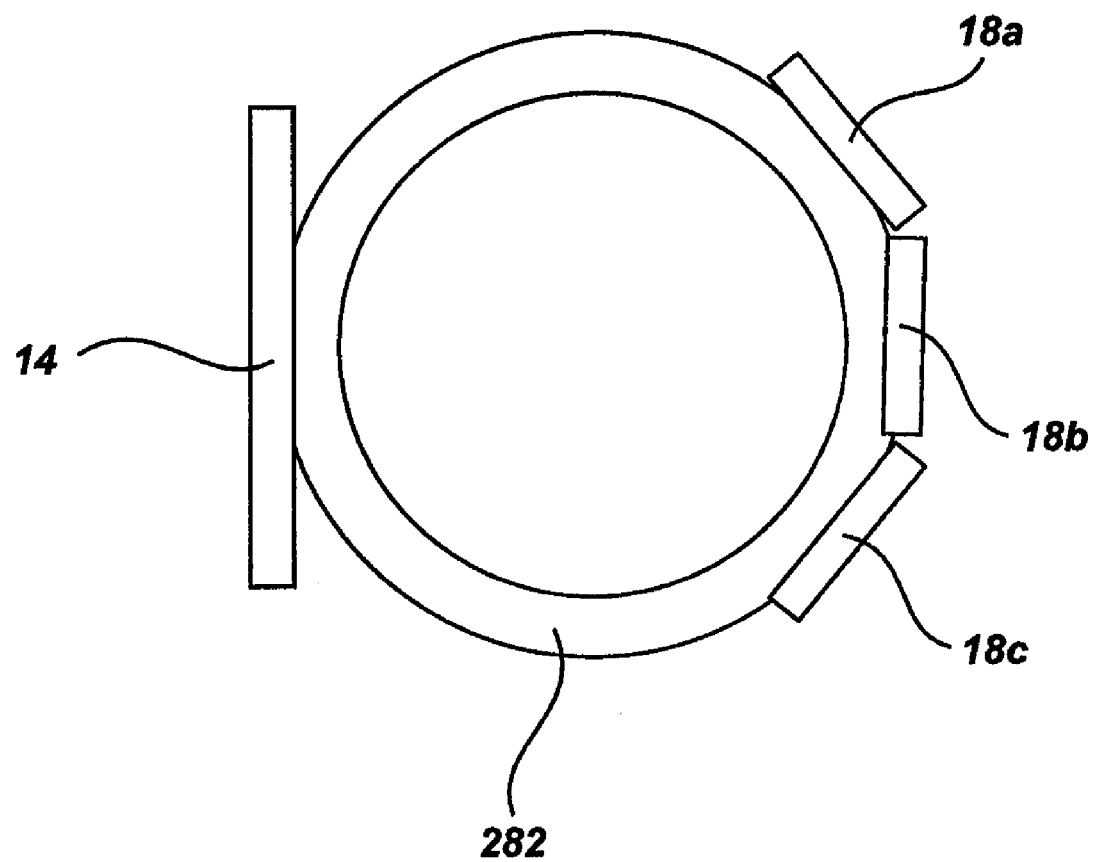
FIG. 11 shows an end view of a sensor configuration for the detectors of the present invention, the sensors being disposed about a fluid transport tube.

Turning now to FIG. 11, a sensor configuration for the air bubble detectors of the present invention is shown. It will be appreciated that it is often more difficult to detect bubbles in a large tube than in a smaller tube. There is often a practical limit to how large a sensor element may be and still perform reasonably well at detecting bubbles. Many medical tubes are about 3-4 millimeters in diameter, and commonly used sensor elements may be about 3 by 5 millimeters. In a larger tube, such as one of 8 or 10 millimeters, as may be used in other applications, the ultrasonic waves passing between the emitter and the receiver may not cover the entire cross section of the tube and a bubble could flow around the region covered by the sensor.

An end view of a larger tube 282 is shown. The sensor elements have been arranged as a single larger emitter 14 and multiple receivers 18a-18c arranged in a concave configuration to better conform to the tubing shape. The array of receivers 18a-18c provides better coverage through the bore of the tube 282. Using an array of receivers may provide additional benefits, such as a stronger indication of a smaller bubble. A smaller bubble may block only a small portion of the signal being received by a larger receiver, but would block a much larger portion of the signal being received by one of the smaller receivers 18a-18c shown here. The system may also be operated with an array of emitters and a single receiver, but may lose some of the advantages of having multiple, smaller receivers. A detector using the sensor array shown in FIG. 11 may be formed as an adapter with a rigid conduit which is connected to the flexible infusion lines or other fluid transport tubes, or may be formed as a clothespin, adjustable channel or fixed channel type housing. A larger tube 282 will typically be flexible enough to be placed into a fixed channel having the sensor configuration shown. However, a movable channel can also be used.

Figure 12:
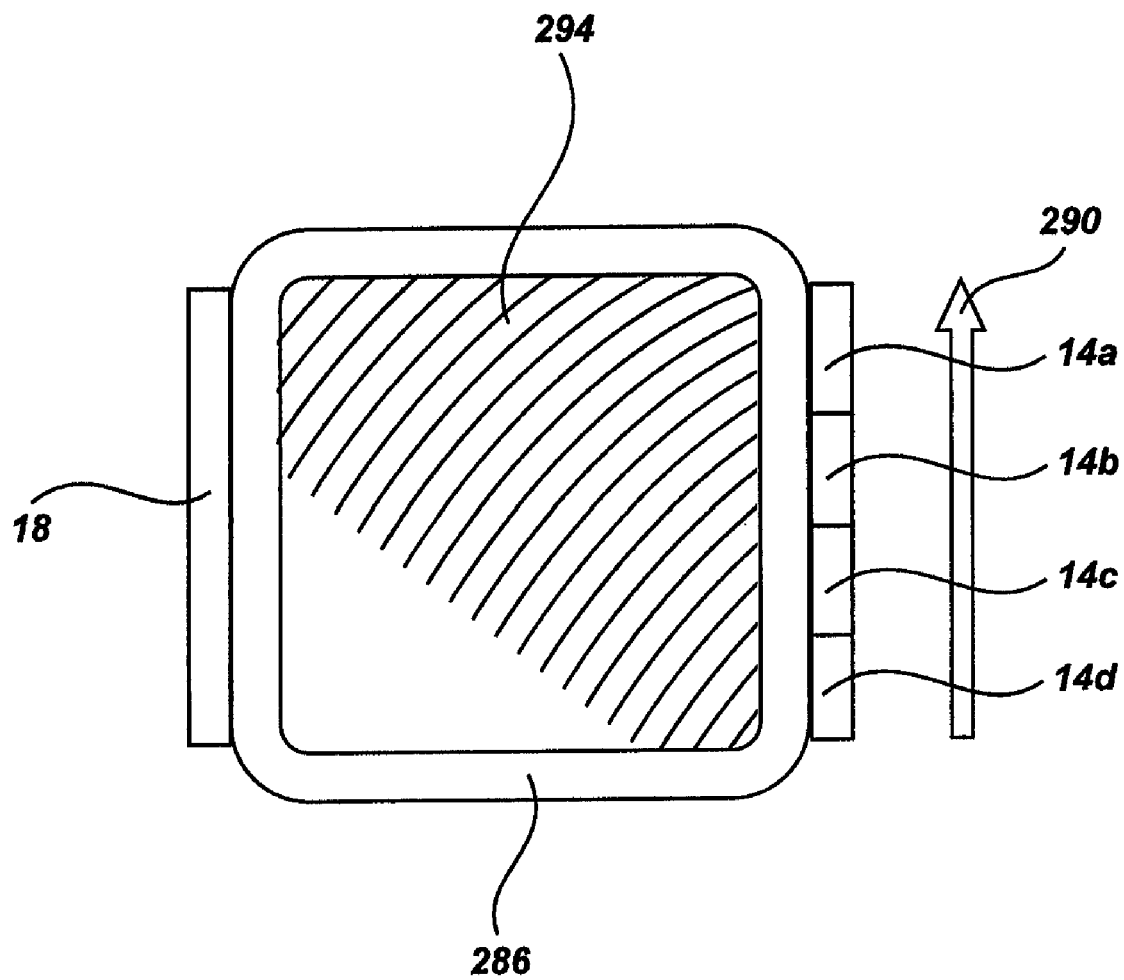
FIG. 12 shows an end view of a sensor configuration for the detectors of the present invention, the sensors being disposed about a fluid transport tube.

Turning now to FIG. 12, another sensor configuration for providing improved sensor coverage in a larger tube is shown. A tube 286 is placed between an array of emitters 14a-14d and a receiver 18 (or an array of receivers). The emitters 14a-14d may be used to emit pulses of ultrasonic frequencies in sequence across the array of emitters, i.e. rapidly sequentially emitting ultrasonic frequencies from one side of the emitter array to the other side of the emitter array. This causes the resulting beam to be directed off towards one side of the bore of the tube 286. As shown, activating the emitters in a sequence from bottom to top (as indicated by arrow 290) will cause the resulting ultrasonic beam 294 to be directed to the top of the tube 286. The emitters 14a-14d may then be activated from top to bottom to aim the ultrasonic beam to the bottom of the tube 286. The detector may be used accordingly to better detect bubbles in the areas of the tube 286 which are not directly between the emitters 14a-14d and receiver 18. The detector electronics will evaluate the signals received to detect changes in the signal caused by a bubble.

Figure 13:
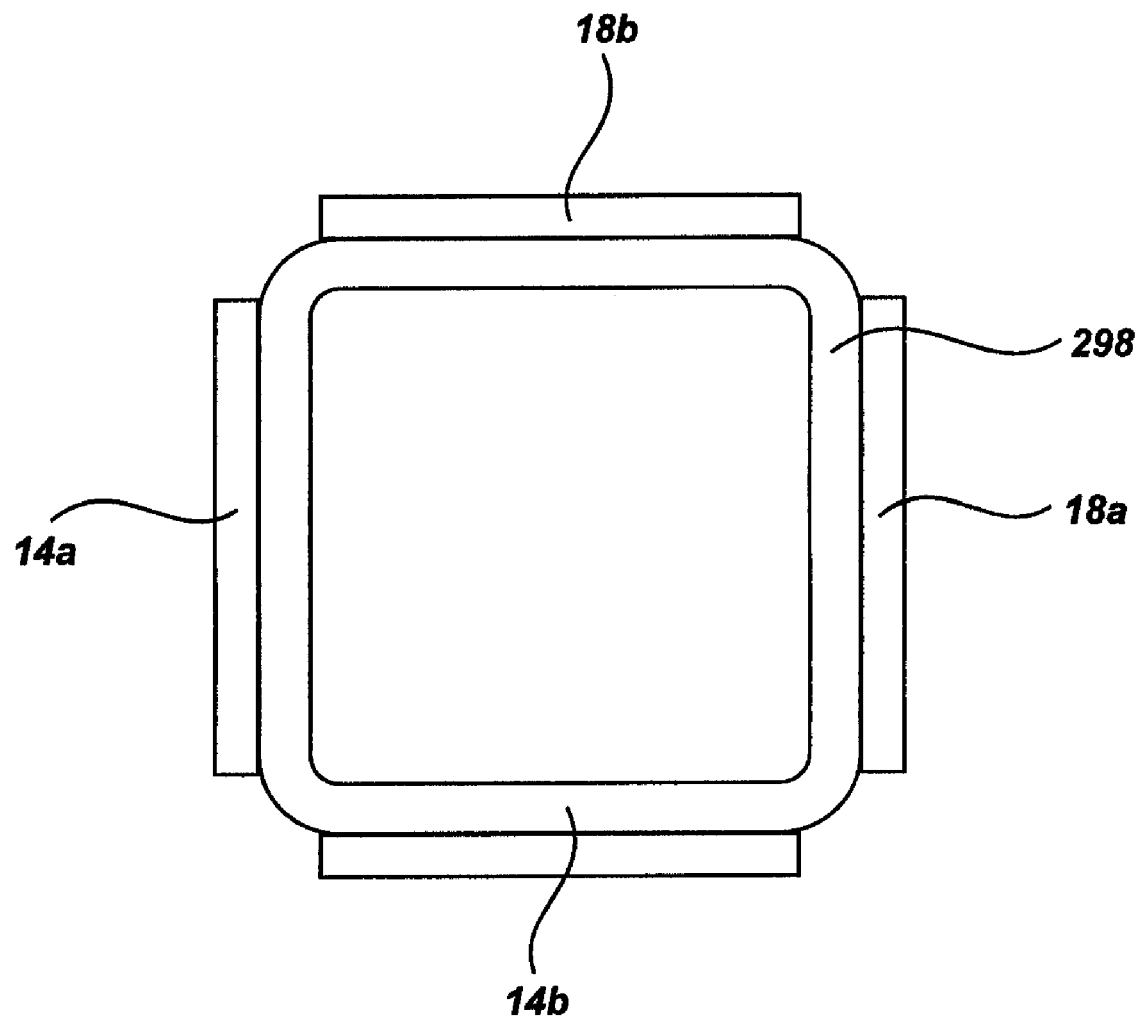
FIG. 13 shows an end view of a sensor configuration for the detectors of the present invention, the sensors being disposed about a fluid transport tube.

Turning now to FIG. 13, another sensor configuration for an air bubble detector is shown. The detector may include a first sensor pair having an emitter 14a and receiver 18a and a second sensor pair having an emitter 14b and a receiver 18b. The first sensor pair and second sensor pair are placed around a tube 298 at approximately a right angle to each other. The use of two sensor pairs may provide better detection of bubbles located along the sides of the tube (away from the center of the tube).

The sensor pairs may be located at the same point along the tube 298, or one sensor may be downstream of the other sensor. Locating the sensors at the same point along the tubing may result in a simpler detector housing (which would typically include a clamshell type door to enclose the tube 298 in the sensor arrays or a clothespin type housing to perform the same). The housing may have both emitters 14a, 14b on one side of the clothes pin or on the housing base and have both receivers 18a, 18b on the other side of the clothes pin or on the housing door. Locating one sensor somewhat downstream from the other sensor could allow the detector to provide flow direction and velocity information based on the time delay between detection of a bubble by one sensor and the other sensor. This may, however, increase the risk somewhat that the bubble may be undetected by the air bubble detector.

Figure 14:
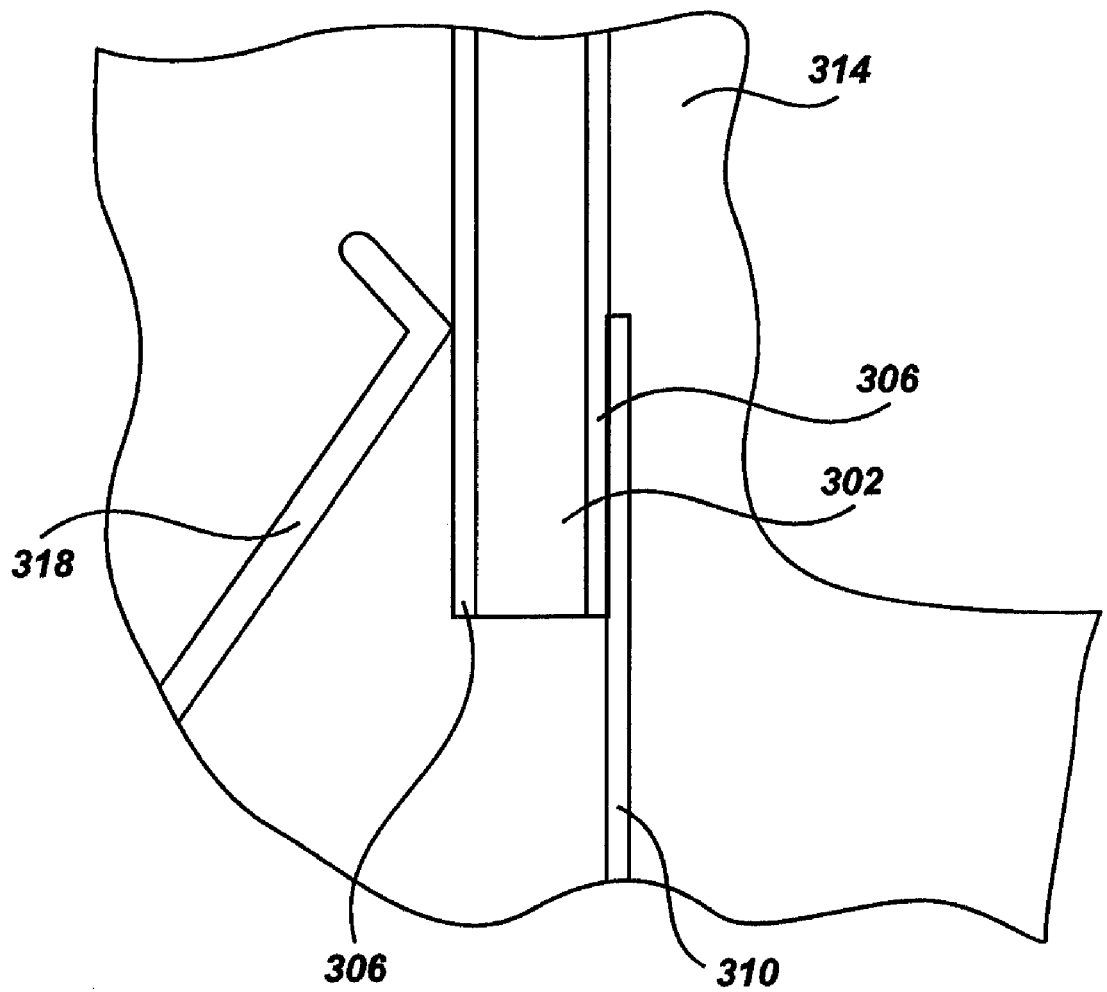
FIG. 14 shows a fragmented end view of a ultrasonic sensor electrical connection for the detectors of the present invention.

Turning now to FIG. 14, a method of forming the electrical contact with the sensor elements is shown. The ultrasonic sensor element 302 (as is used for emitters 14 and receivers 18 discussed herein) is typically a thin ceramic chip with thin layers of silver or gold 306 deposited on the faces thereof. The electrical contact to the sensor element 302 typically consists of two small wires soldered to both sides of the element (soldered to conductive layers 306). In order to make an ultrasonic air bubble detector which is more resistant to shock, vibration, etc. the electrical contacts with the sensor element 302 may consist of an electrical contact 310 attached to the housing 314 and a spring 318. The spring 318 presses the sensor element 302 against the electrical contact 310 such that the spring and electrical contact make the two necessary electrical contacts on the two sides of the sensor element. Such a method of making electrical contact with the sensor element 302 may be used in any of the air bubble detector designs.

Figure 15:
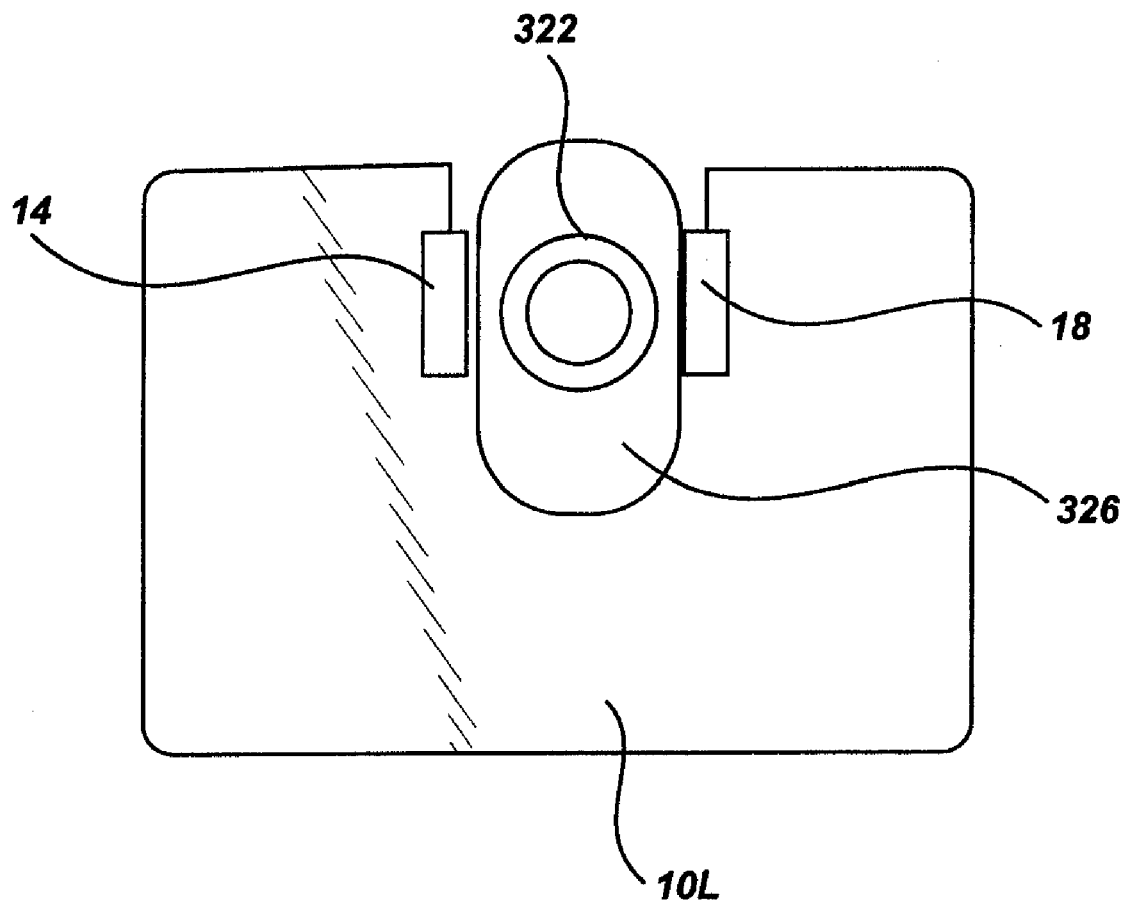
FIG. 15 shows an end view of a detector of the present invention with a fluid transport tube disposed therein.

Turning now to FIG. 15, an air bubble detector of the present invention is shown as may be used to detect fluid contamination in an air line. The air bubble detector 10L may utilize any of the housing and sensor designs shown herein. The air carrying tube 322 is placed between an emitter 14 and receiver 18. As air carrying lines 322 are often rigid tubes, a compliant sleeve 326 may be disposed around the tube, or the sensor may have a compliant surface covering the side walls of the detector channel.

Figure 16:
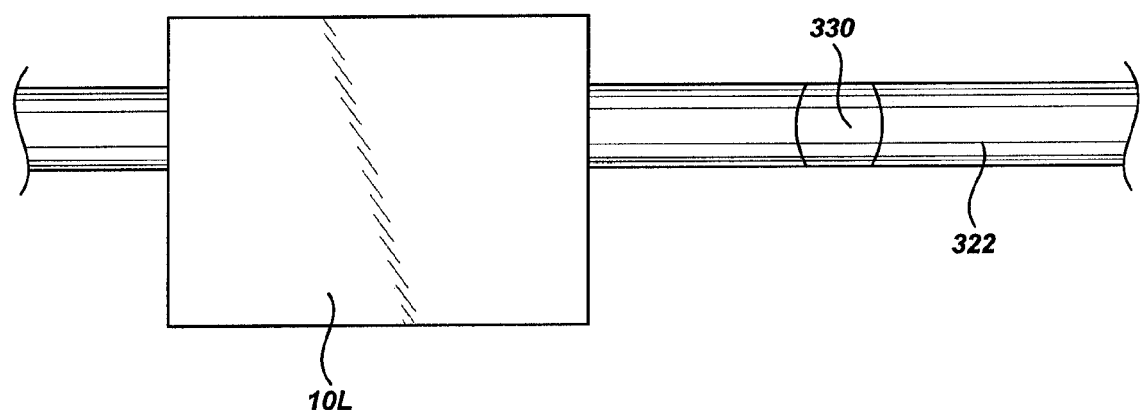
FIG. 16 shows a schematic diagram illustrating a use of the detectors of the present invention.

FIG. 16 shows a side view of the sensor of FIG. 15. Often, industrial air, gas, or vacuum lines comprise a larger main distribution line and smaller lines which branch off to individual pieces of machinery or parts of a machine. Droplets of liquid may be carried into these smaller lines and interfere with the operation of the machine. The detector 10L may be used to detect the presence of liquid in the smaller tubes 322. A drop of liquid 330 which has entered tube 322 will be carried past the detector 10L. The detector will detect a change in the transmission of the ultrasonic signal which passes from the emitter 14 to the receiver 18 (typically an increase in the transmission as the air in the tube will not significantly transmit the ultrasonic signal). The detector 10L, or the equipment to which the detector is connected, will be programmed to determine when a liquid drop has passed by the detector and what the appropriate response is, and may then initiate that response.

According to the present invention, an air bubble detector may be used to detect the presence of foreign objects in any fluid, so long as the foreign object has a sufficiently different ability to transmit an ultrasonic signal than that of the bulk fluid. Thus, the fluid may be gasses or liquids, and the foreign object may be gasses, liquids, and solids (such as precipitates or coagulated materials) which are found in the bulk fluid. A foreign object which sufficiently improves or impedes the transmission of ultrasonic signals through the bulk fluid will cause a measurable difference in the output signal from the detector. The detector circuitry and programming, or that of a machine to which the detector is connected, may be configured to recognize foreign objects of importance and report the same and/or take a predetermined action.

Figure 17:
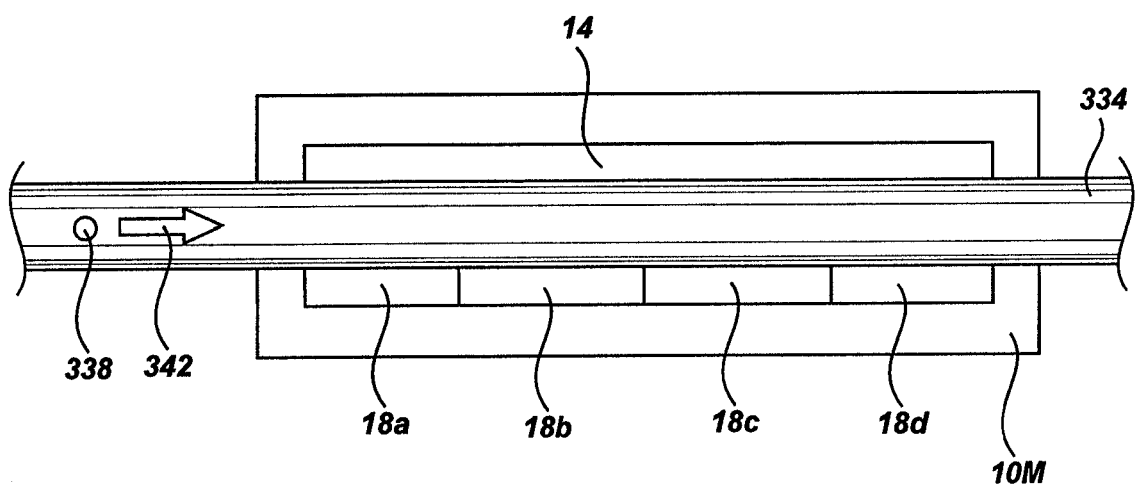
FIG. 17 shows a top view of a sensor configuration for the detectors of the present invention and a method of using the detectors of the present invention with a fluid transport tube disposed therein.

FIG. 17 shows a top view of a detector 10M having another sensor configuration. The detector 10M includes an emitter 14 and a plurality of smaller receivers 18a-18d. A tube 334 is placed in the detector 10M between the emitter 14 and receivers 18a-18d, typically in a channel formed in the detector. Each of the receivers 18a-18d may be connected individually to the detector control circuitry so as to provide separate bubble detection signals to the detector. The sensor configuration shown is advantageous as it allows the detector 10M to provide more accurate detection of smaller bubbles and also allows the detector to provide information about the fluid flow through the detector.

The detector 10M can more accurately detect smaller bubbles than a detector having a single large receiver because the same bubble will block a larger percentage of the signals to the individual smaller receiver 18. If four smaller receivers 18a-18d are used instead of a single larger receiver having the same total area, the percentage of the ultrasound signal which is blocked from reaching the smaller receiver chip is about four times larger than the percentage of the signal which is blocked from the larger single receiver chip. For example, if a single larger receiver chip is used with a cross-sectional area of 100 units and a small bubble blocks the ultrasonic signal from reaching 5 units of the receiver chip area, the bubble has blocked 5 percent of the signal. If the single larger receiver chip is replaced by four smaller receiver chips 18a-18d which each have a cross-sectional area of 25 units, the total area of the receivers still equals 100 units. The same bubble passing through the tube would block 5 units of area as it passes by each of the receivers 18a-18d. That 5 units of area is, however, 20 percent of the area of the smaller receivers 18a-18d. The same bubble blocks 20 percent of the signal to each receiver 18a-18d as it passes by. The detector 10M is thus better able to detect smaller bubbles as the change in the signal produced by the receivers 18a-18d is greater.

The detector 10M is also able to provide additional information about the fluid flow. A bubble 338 flowing through the detector 10M in the direction of arrow 342 will pass by receivers 18a-18d in sequence. The linear velocity of flow through the tube 334 may be determined by dividing the width of the receivers 18a-18d by the time delay between the signals produced by each receiver. Typically, the time delay between each receiver will be about the same, such that receiver 18a will produce a signal, receiver 18b will produce a signal after a short time delay, receiver 18c will produce another signal after another short time delay, and receiver 18d will produce another signal after another short time delay. The time delays between the signals may be averaged to determine an average speed, or the shortest time delay may be used as the bubble may travel at a slower velocity than the fluid if it is moving along the surface of the tube 334 and being slowed somewhat.

Once a linear flow velocity is determined, the volumetric flow rate may be determined by multiplying the linear flow velocity by the cross-sectional area of the tube 334. The detector 10M may also provide information about the direction of flow by determining in what order the receivers produce roughly equivalent signals corresponding to one particular bubble. A series of signals produced starting from receiver 18a and continuing through receiver 18d indicate flow from left to right as indicated by arrow 342. A series of signals which begin in receiver 18d and continue through receiver 18a indicate that the fluid flow is from right to left.

The use of multiple receivers 18a-18d provides additional advantages. The detector 10M may be programmed to ignore unusual signals which are produced by one receiver and not by the remaining receivers, as that may indicate a receiver failure or another problem with the receiver such as moisture interfering with proper operation of the detector. The detector 10M may be programmed to require that at least two receivers 18a-18d detect a bubble in order to verify that a bubble has been detected. Additionally, the use of multiple receivers 18a-18d provides redundant sensing which may increase reliability in higher flow rates or when detecting smaller bubbles.

Figure 18:
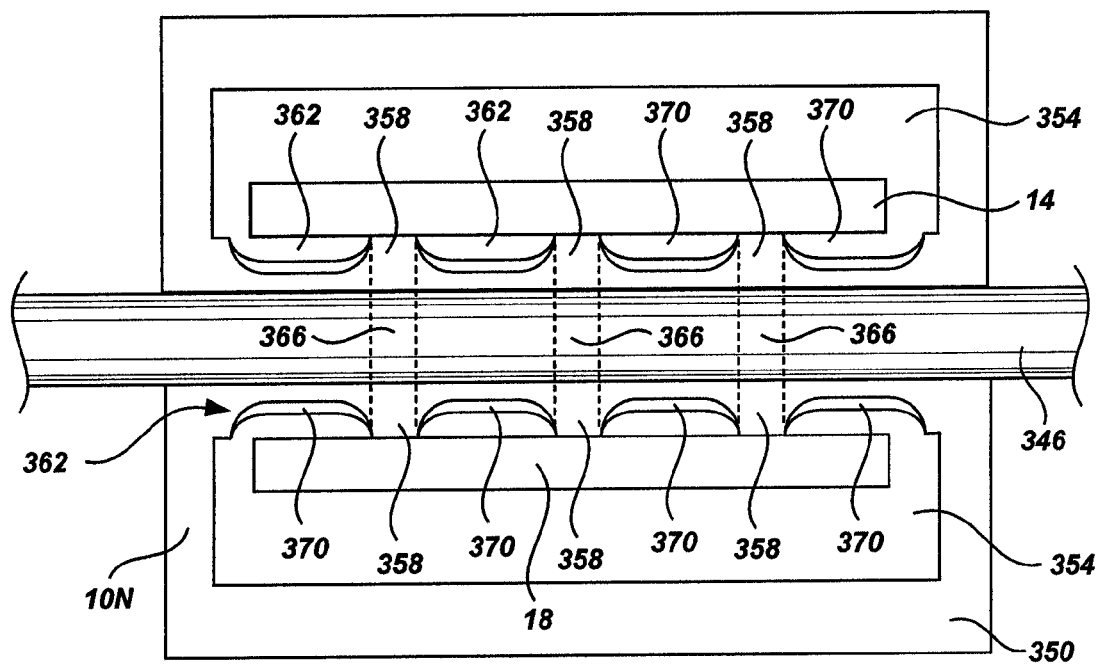
FIG. 18 shows a top view of a sensor configuration for the detectors of the present invention with a fluid transport tube disposed therein.

FIG. 18 shows a top view of another sensor configuration for the detectors of the present invention. A tube 346 is disposed in a channel in the detector 10N. The detector housing 350 has slots 354 formed therein for receiving the emitter 14 and receiver 18. The slots 354 are typically formed from the bottom of the housing 350 such that they are typically not exposed when the detector 10N is in use. The emitter 14 and receiver 18 are positioned in the slot 354 and glued in place with a glue which transmits the ultrasonic signals. The slots 354 may be formed with a number of raised pedestals 358 which form ultrasonic transmission zones, i.e structures that transmit the ultrasonic signals. It will be appreciated that ultrasonic signals are not well transmitted through air, but may be transmitted with little noise through other materials. The term pedestal is not intended to define any particular shape, but rather to define a raised structure which connects the emitter(s) and/or receiver(s) to the conduit. The pedestals 358 contact the emitter 14 or detector 18 and help transmit the ultrasonic signals therebetween.

The areas adjacent the pedestals, as indicated at 362 (only a few are labeled for clarity), are recessed so as to not contact the emitter 14 and receiver 18. Each of these areas creates an air gap between the housing 350 and emitter 14 or detector 18 which blocks the ultrasonic signals from passing therethrough. Thus, the use of pedestals 358 creates a number of bubble detection areas 366 which are smaller than the emitter 14 or detector 18. It will be appreciated that if the glue used to adhere the emitter 14 and receiver 18 to the housing 350 fills in some of the recessed areas 362, the size of the pedestals 358 may effectively be changed. Thus, a material 370 which blocks the ultrasonic signals may be placed so as to fill or cover these recesses 362. The material 370 may be a material which contains a sufficient air content such as an air impregnated latex. The material 370 may be applied with a syringe or the like and allowed to dry before installation of the emitter 14 and receiver 18. The smaller bubble detection areas 366 created by the pedestals 358 are better suited for sensing smaller bubbles and provide redundant sensing of bubbles. Additionally, flow velocity (but not direction) may be determined from the time delay between the signals generated by a bubble passing through the bubble detection areas 366 and the centerline distance between the pedestals 358.

Figure 19:
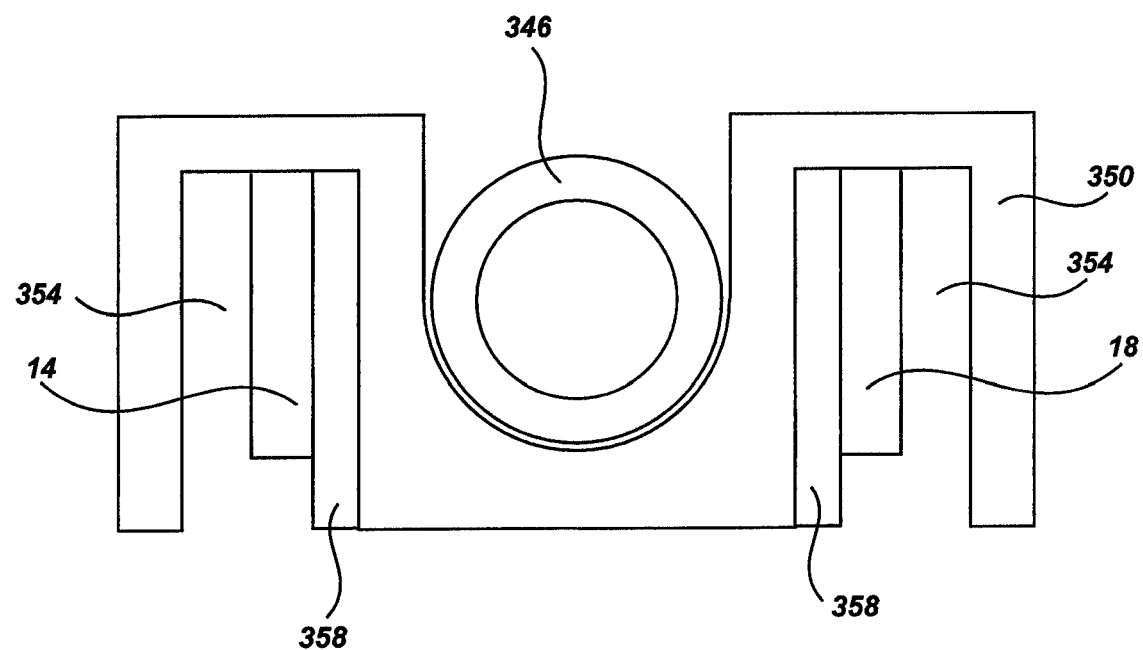
FIG. 19 shows an end view of a sensor configuration for the detectors of the present invention with a fluid transport tube disposed therein.

FIG. 19 shows a partially cut away view of the detector 10N of FIG. 18. It can be seen how the slots 354 allow the emitter 14 and receiver 18 to extend upwardly to a sufficient degree so as to pass a signal through the entire cross-section of the tube 346. The pedestals 358 will typically also typically extend upwardly across the face of the emitter 14 and receiver 18.

Figure 20:
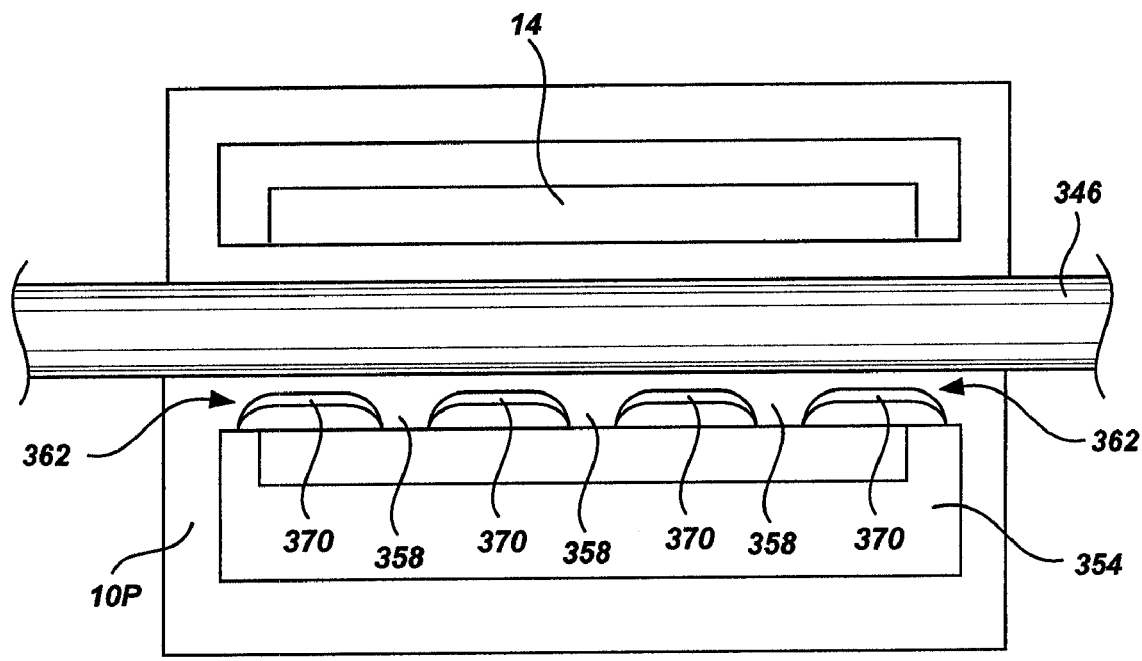
FIG. 20 shows a top view of a sensor configuration for the detectors of the present invention with a fluid transport tube disposed therein.

FIG. 20 shows a detector 10P which is similar to that of FIGS. 18 and 19, but which utilizes pedestals 358 adjacent the receiver 18 and not the emitter 14 (or alternatively adjacent the emitter 14 and not the receiver 18). The housing 350 typically is similarly formed with recessed areas 362, ultrasonic masking 370, etc. as discussed above. The use of pedestals on only one side of the housing 350 may provide similar performance to the detector 10N shown in FIG. 18, but may be easier to manufacture by using pedestals on only one side of the housing.

Figure 21:
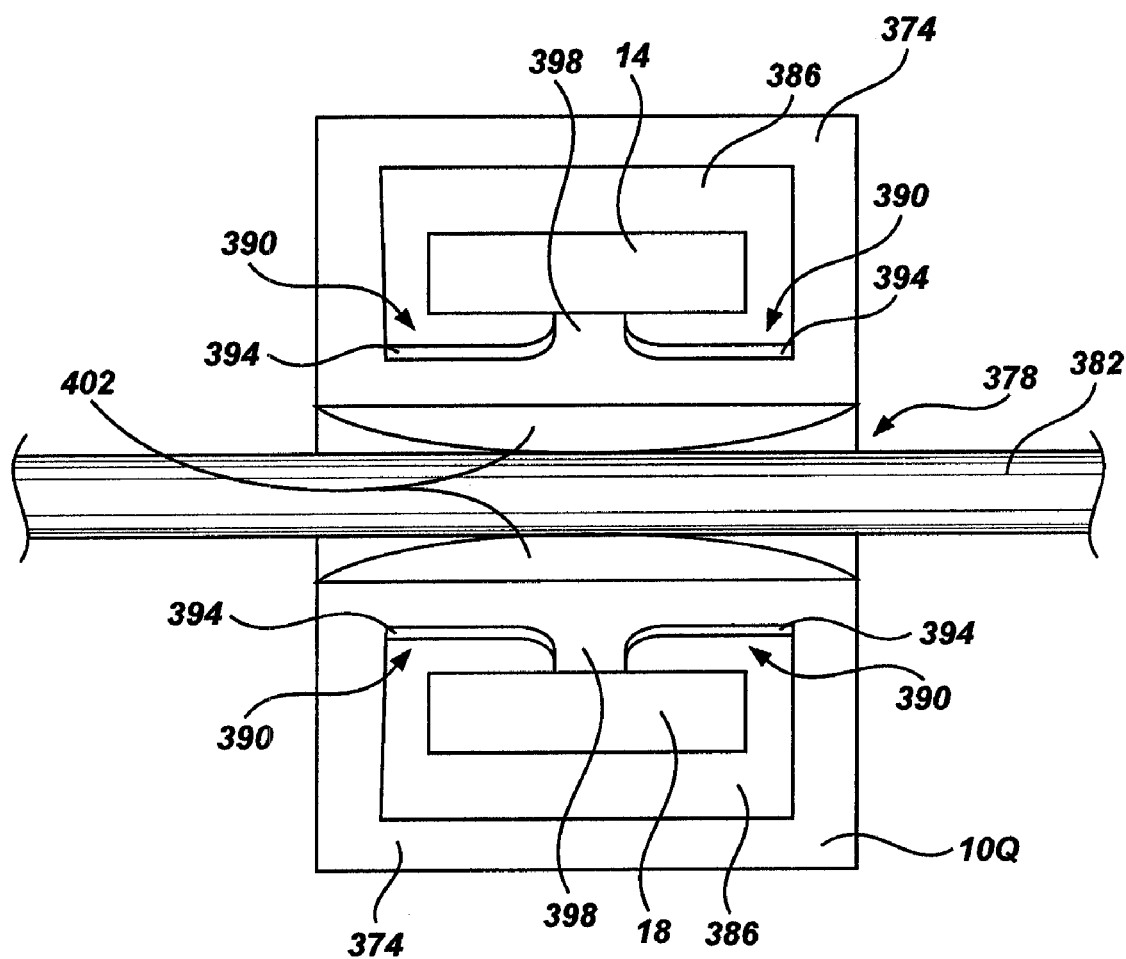
FIG. 21 shows a top view of a sensor configuration for the detectors of the present invention with a fluid transport tube disposed therein.

FIG. 21 shows another detector 10Q of the present invention. The detector 10Q includes a housing 374 which forms a channel 378 to receive a tube 382. The housing 374 includes slots 386 which receive the emitter 14 and receiver 18. The slots may be formed with recessed areas 390 and ultrasonic masking material 394 which block the transmission of the ultrasonic frequencies, and pedestals 398 which conduct the ultrasonic frequencies. As discussed before, the pedestals 398 are raised plateaus in the side of the slot 386 which contact the emitter 14 or receiver 18 and transmit the ultrasonic frequencies, while the air gaps or foamed mask materials block the ultrasonic frequencies. The emitter 14 and receiver 18 are typically glued to the pedestals 398 with a type of glue which conducts the ultrasonic frequencies. As discussed earlier, the detector 10Q may include compliant faces 402 disposed in the pedestal for improving the ultrasonic coupling with a rigid tube, or may omit the compliant faces for a soft tube. The compliant faces 402 may be formed from a thermoplastic elastomer, polyurethane, etc.

The pedestals 398 (and those discussed earlier) provide several advantages. As discussed above, multiple pedestals may provide redundant sensing or may provide additional flow information. The use of a single pedestal in a detector may allow the customization of the detector while using a standard size of emitter 14 and receiver 18. In many situations, it is desirable to detect smaller bubbles. This is advantageously achieved by limiting the effective sensing area of the emitter 14 and/or receiver 18 such that the smaller bubbles generate a larger and more easily detectable change in the detector signal. This also may be achieved by using smaller sensor elements (emitter 14 and receiver 18). The sensor elements would typically be the same overall length as they should extend upwardly across the bore of the tube, but would be narrower to present a narrow bubble sensing window such as is created by the pedestals 398.

It is, however, disadvantageous to use such customized sensor elements. The smaller elements may be more difficult to handle, attach wire leads, install, etc. Additionally, each different air bubble detector may require different customized sensor elements, making it more difficult and expensive to stock the various sensor elements. The use of pedestals 398 as discussed is thus advantageous as a standard size of sensor element may be adapted to many different tube sizes and may be adapted to vary the lower threshold of bubble size which is detected. Additionally, the sensor housing 374 may be a standard piece which is easily customized for different applications. The slots 386 may be molded in the housing 374 without forming the recesses 390 or pedestals 398, and these may be cut into the side of the slots afterwards to create a customized detector from a standard housing. The configuration shown is also advantageous because the transmission path between the emitter 14 and receiver 18 is determined by the pedestals 398 and may be tightly controlled in manufacturing, and does not depend on exact placement of the emitter and receiver, as these are larger than the pedestals.

Figure 22:
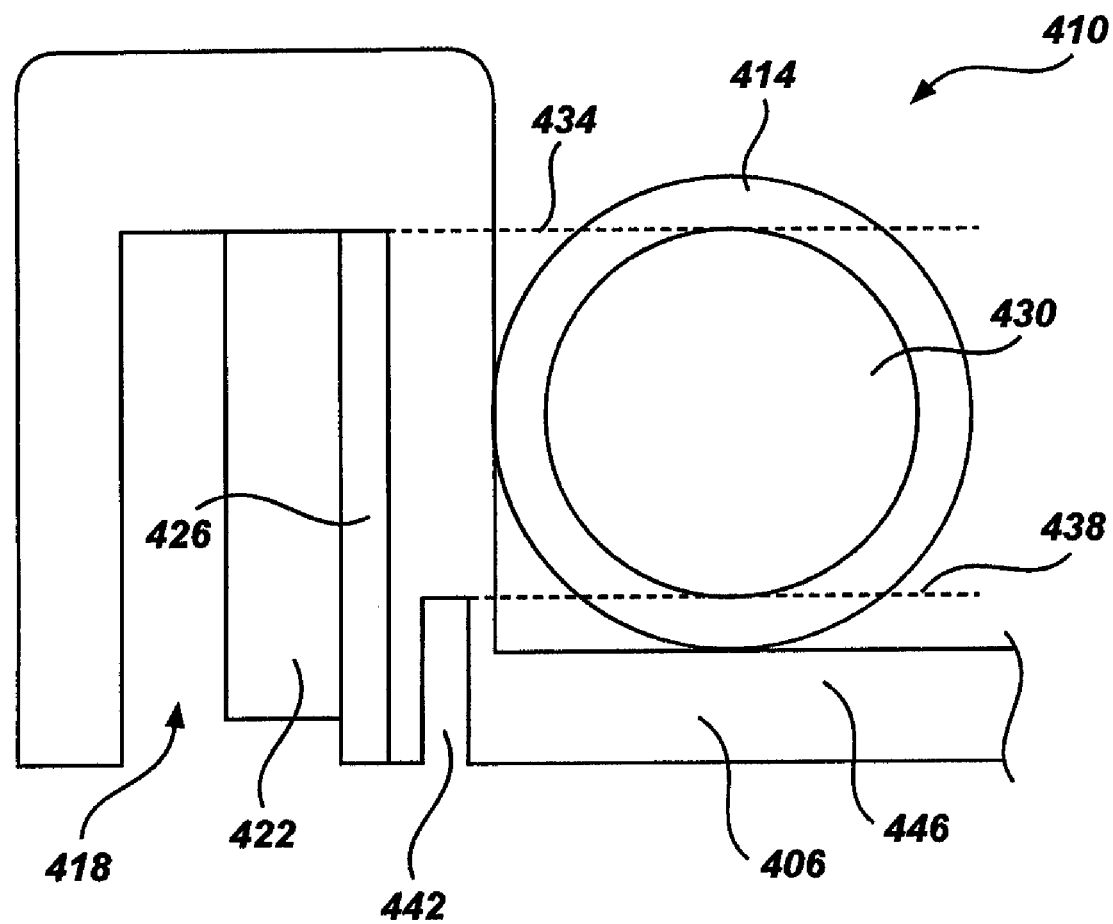
FIG. 22 shows a fragmented end view of a sensor configuration for the detectors of the present invention with a fluid transport tube disposed therein.

FIG. 22 shows a partial cut-away view of a detector housing such as those shown in FIGS. 18-21, and as may be used with any of the sensor configurations shown herein. The housing 406 forms a channel 410 to receive a tube 414. A slot 418 is formed in the bottom of the housing 406 to receive a sensor element 422 (an emitter 14 or receiver 18). The slot 418 has been formed with an pedestal 426 similar to those shown previously. The pedestal 426 will typically extend vertically along the slot 418 so as to cover the cross section of the tubing 414. The term pedestal is used for the pedestal-shaped (or other shaped) structure 426, as the structure is used to transmit the ultrasonic signals. It is appreciated that an air gap blocks the signals, and solid material would transmit the signals. The pedestal 426 functions similar to an pedestal in a camera, allowing the ultrasonic signals to pass through the area defined by the pedestal.

According to the present invention, the transmission pathway for the ultrasonic signals may be limited so as to substantially pass only through the bore 430 of the tubing 414, as indicated by the dashed lines 434, 438. The depth of the slot 418 in the housing 406 may be controlled to place the upper edge of the sensor element 422 at about the same height as the upper edge of the tube bore 430 such that the upper edge of the ultrasonic signal pathway is defined by dashed line 434. A slot 442 may be formed in the housing 406 to block the ultrasonic signals from the lower portion of the sensor element 422 such that the ultrasonic signals above the slot 442 pass through the tubing 414. In such a manner, the ultrasonic signals may be limited to only passing through the bore of the tubing. If necessary, the depth of the slot 442 could be adjusted by filling it with a material which will transmit the ultrasonic signal to a level providing the desired boundary for the signal. It will be appreciated that, in use, the tubing 414 would typically be pressed against the sides of the channel 410 such that air gaps are not present between the tubing and the channel in the area of ultrasonic signal transmission.

It is advantageous to limit the ultrasonic signals to passing through the bore 430 of the tube 414 to prevent alternate routes of signal transmission. It is appreciated that ultrasonic signals would be transmitted through the base 446 of the housing 406 if not blocked from doing so. It has also been determined that ultrasonic signals may pass above the tube 414 if liquid is present on the surface of the tube between the sensor elements 422, and if the sensor elements 422 extend above the tube 414, or tube bore 430. The ultrasonic signals are transmitted in a substantially straight line and do not spread much. As such, controlling the position of the top of the sensor element 422 relative to the top of the bore 430 and limiting the transmission area of the bottom of the sensor element with a slot 442 is an effective method of allow ultrasonic signals to pass only through the bore 430 of the tube 414.

The above described detector configuration provides an effective method for preventing stray ultrasonic signals and for preventing liquids such as condensation or spills from eliminating the effectiveness of the sensor. It is appreciated that the bubble detectors function by detecting the change in the strength of the signals which are received by the receiver 18 (transmitted from the emitter 14) due to a bubble blocking some of those signals. If ultrasonic signals are able to pass through the base 446 of the housing 406, or above the tubing due to liquid contamination, the receiver 18 will receive additional signals from the emitter 14 and the bubbles may go undetected due to their lessened effect on the signal, or due to their no longer bringing the received signal across a predetermined threshold. It is appreciated that slots 442 could be used on both the top or bottom of the sensor element 422, and that the position of the sensor element 422 may be controlled on the top or bottom of the sensor element. To accommodate different sizes of tubes 414, the depth of the slot 418 and slot 442, as well as the depth and position of the channel 410 may all be varied.

Figure 23:
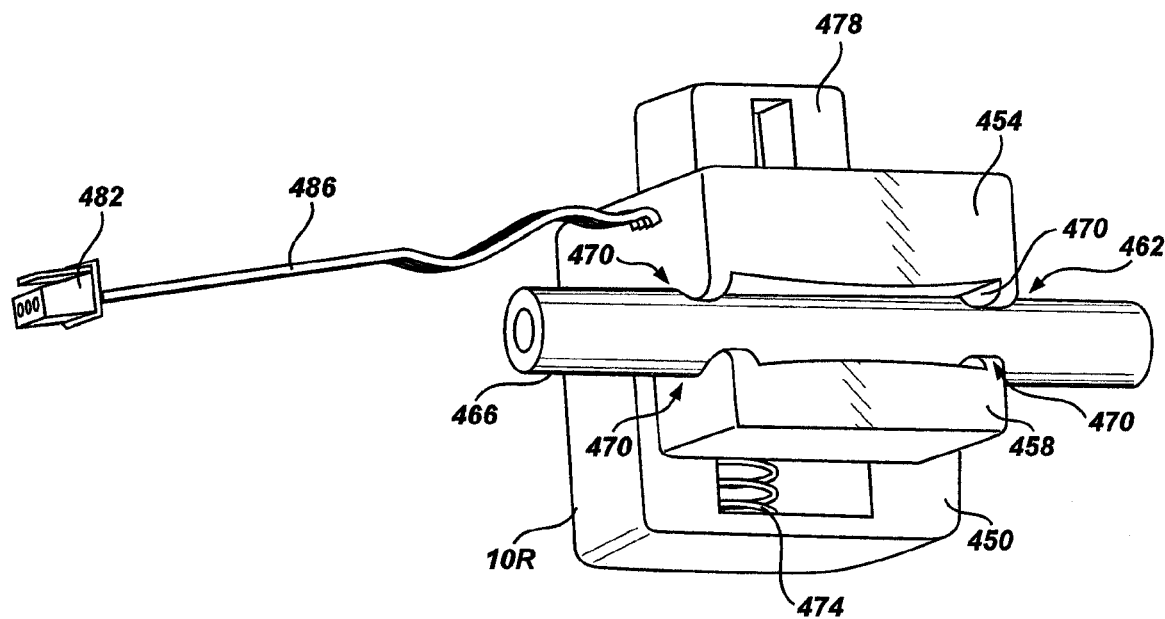
FIG. 23 shows a perspective view of a detector of the present invention.

Turning now to FIG. 23, a perspective view of a detector 10R according to the present invention is shown. The detector 10R has a linearly adjustable channel type housing 450. The housing 450 includes a fixed arm 454 and a linearly slidable arm 458, and forms a channel 462 between the arms. The tube 466 is held in the channel 462. The channel 462 may include V-shaped or U-shaped notches 470 or the like to keep the tube 466 properly aligned in the channel. A spring 474 may be used to bias the slidable arms 458 towards the fixed arm 454 to narrow the channel 462 and to properly close the channel around the tubing 466, holding the tubing securely against the walls of the channel for good ultrasonic signal transmission. The slidable arm 458 may include or be attached to a button 478 which protrudes past the housing 450 and allows a user to open the channel 462 against the bias of the spring 474 to load the tube 466 in the channel. It can bee seen how the detector 10R may be provided with an electrical connector 482 and cord 486 to allow the detector to be connected to outside devices such as a pump, controller, emergency shut off valve, etc.

Figure 24:
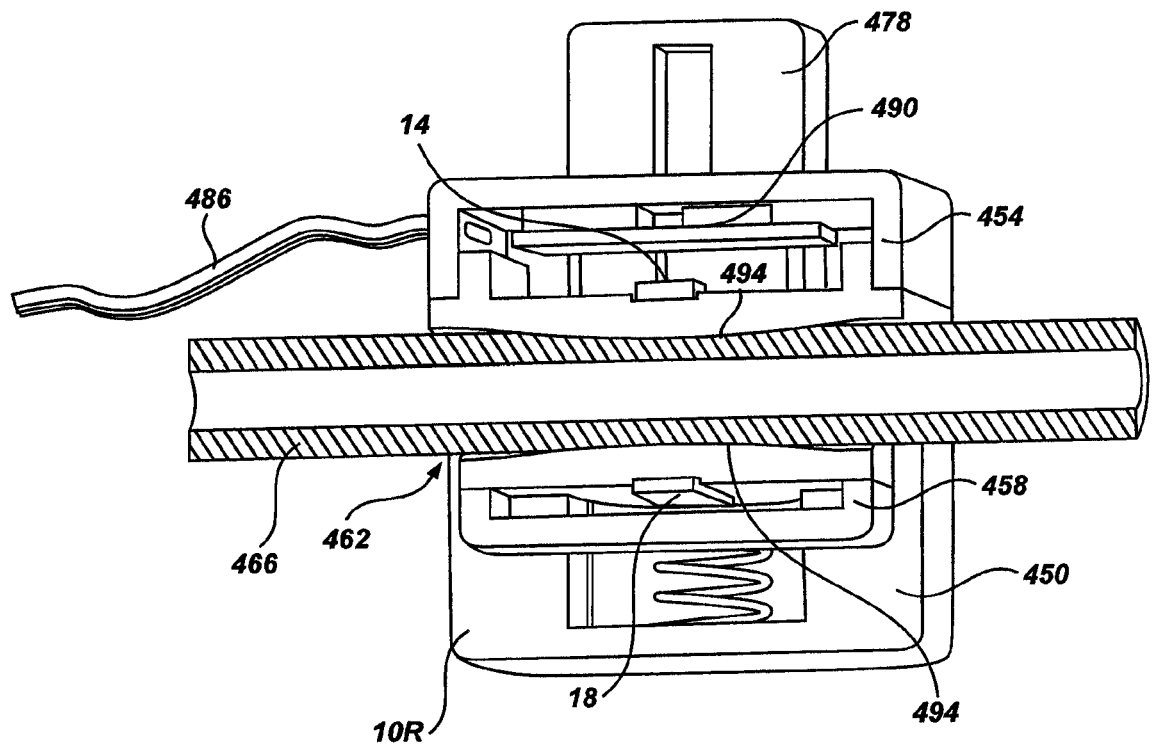
FIG. 24 shows a cutaway perspective view of a detector of FIG. 23.

FIG. 24 shows a cutaway view of the detector 10R. The detector 10R has been cut across the center of the tube bore. It can be seen how the channel 462 may include tube engagement surfaces 494 such as dome shaped or raised surfaces for engaging a soft tube or soft surfaces for engaging a rigid tube. One or more emitter 14 and receiver 18 are included and may be placed according to the various different configurations shown previously. The detector 10R may typically include internal circuitry 490 as has been discussed to allow the detector to internally control the emitter 14 and receiver 18 and to process the signals from the emitter and receiver. As such, the detector 10R may be used universally as it may be connected to other devices which do not have the necessary circuitry or programming to control the detector and process the signals. The detector 10R may simply provide the desired processed signals to the device, such as a signal indicating the presence of a bubble, size of a bubble, a stop signal, etc.

Figure 25:
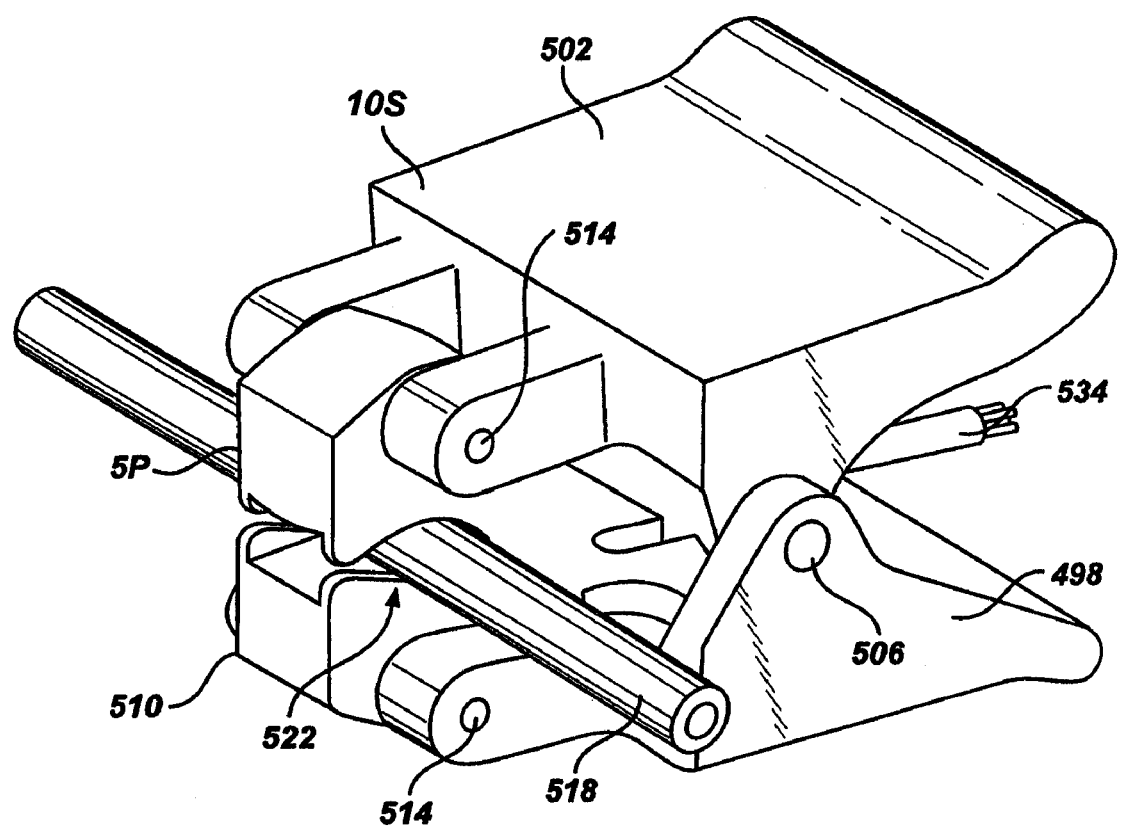
FIG. 25 shows a perspective view of a detector of the present invention.

FIG. 25 shows a perspective view of a clothespin type detector 10S. The detector 10S has a first arm 498 and a second arm 502 which are attached together at a pivot 506. Two sensor mounts 510 are attached to the arms 498, 502 at pivots 514. A tube 518 is held between the sensor mounts 510. The sensor mounts 510 may include V-shaped or U-shaped notches 522 or grooves to properly locate the tube 518 and to secure the tube in the detector 10S.

Figure 26:
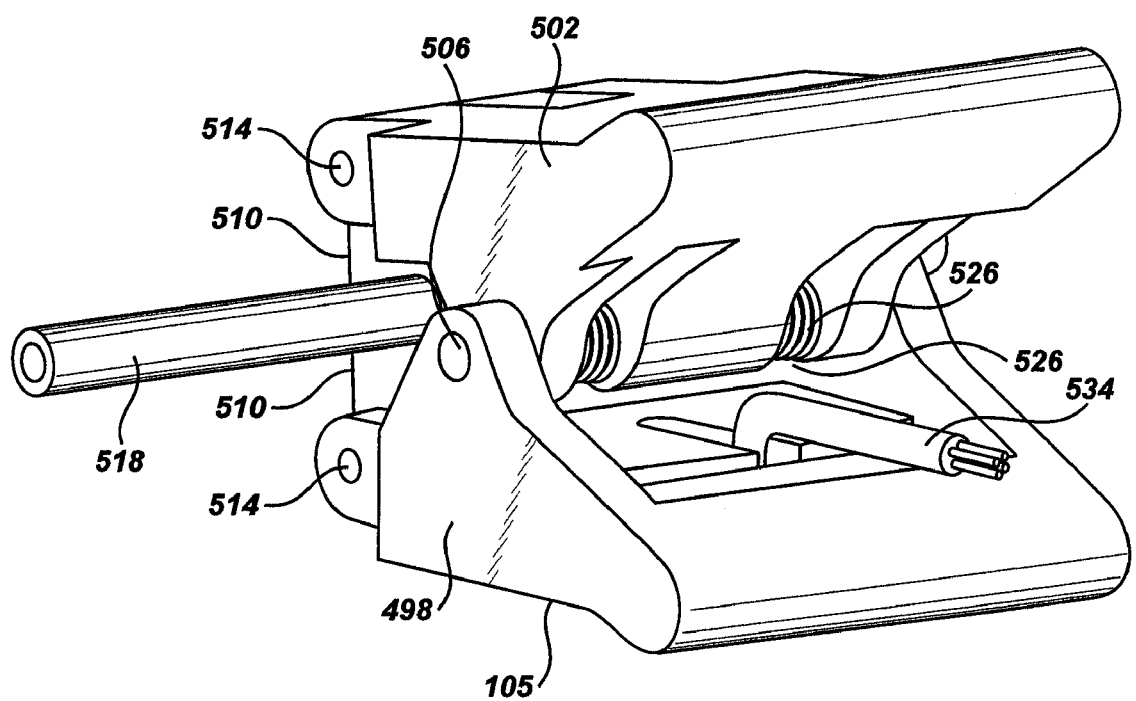
FIG. 26 shows a rear perspective view of a detector of FIG. 25.

FIG. 26 shows a rear perspective view of the detector 10S, illustrating how one or more springs 526 are used to bias the detector in a closed position by holding the sensor mounts 510 against the tube 518. The pivots 514 allow the sensor mounts 510 to be properly aligned with respect to each other to provide good signal transmission through various different sizes of tube 518, allowing the detector 10S to be used universally with different sizes of tubes. Also shown in FIG. 26 is a communications cable 534 for transmitting power, data signals, etc. to and from the detector.

Figure 27:
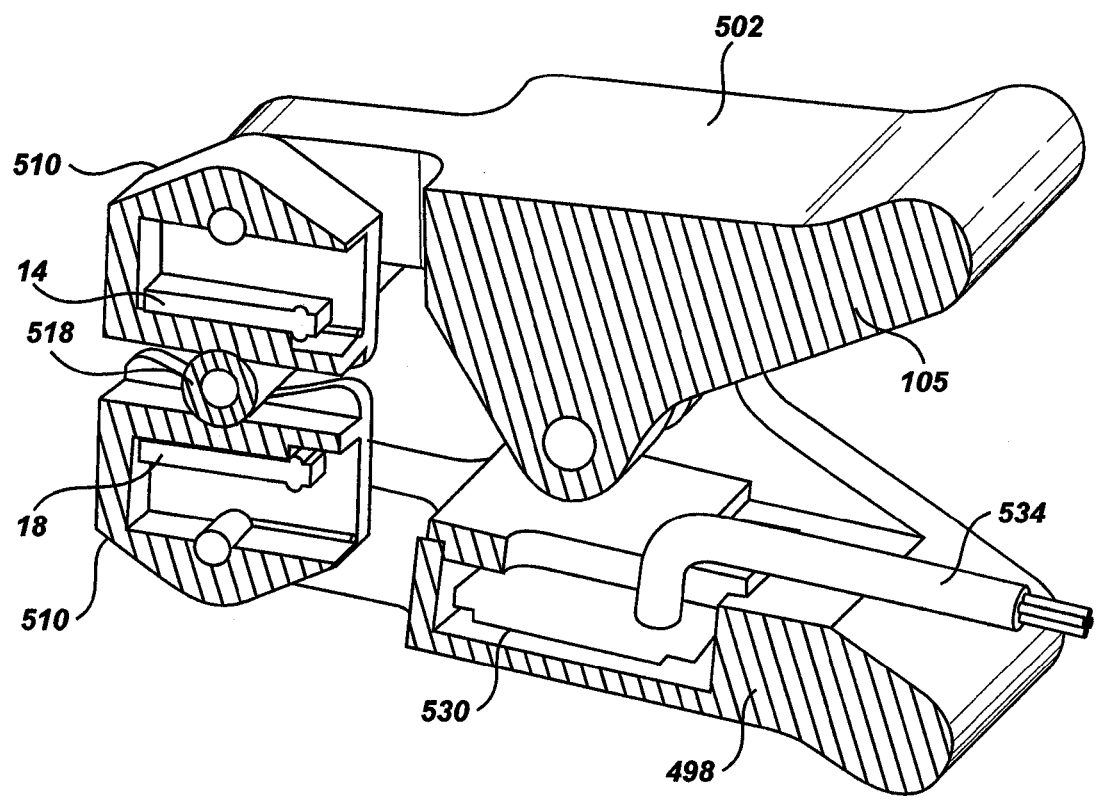
FIG. 27 shows a cutaway perspective view of a detector of FIG. 25.

FIG. 27 shows a cross-sectional view of the detector 10S, illustrating how the emitter 14 and receiver 18 are placed in the sensor mounts 510 so as to transmit a signal through the tube 518. The emitter 14 and detector 18 may be configured according to any of the various emitter/detector configurations shown previously. The detector 10S typically includes electronics 530 to operate the detector 10S, and may process the signals as has been discussed to allow the detector to be used universally with various different types of equipment, valves, etc. The detector will thus have an electrical/communications cord 534 and connector (not shown) to facilitate the same.

In the above disclosure, the various aspects of the air bubble detectors of the present invention are disclosed separately for clarity. Thus, the various types of housing, sensor configurations, ultrasonic signal pedestals and limiting slots, etc. are all disclosed separately for clarity in illustrating each part of the detector. It will be appreciated that the various separate structures may be combined together, such as combining the various types of housings with the various types of sensor configurations, and using the pedestals and ultrasonic beam limiting slots with the various different sensor configurations and housing types. Thus, the various sensor configurations, pedestals, beam limiting slots, etc. should be considered as being taught as a potential part of each housing style.

There is thus disclosed an improved universal air bubble detector. It will be appreciated that numerous changes may be made to the present invention without departing from the scope of the appended claims.

What is claimed is:

1. An air bubble detector for detecting the presence of air in a conduit comprising:
   an air bubble sensor having at least one emitter and at least one receiver, and
   an adjustment mechanism for enabling the emitter and the receiver to be moved toward and away from each other to thereby accommodate conduits of different sizes, the emitter and the receiver being attached to the adjustment mechanism so that the emitter and the receiver maintain alignment with one another so that a signal transmitted from the emitter is properly received by the receiver for any of a plurality of different conduit sizes;
   a plurality of emitters disposed in an array on one mount and a plurality of receivers disposed in an array on a second mount;
   a controller for selecting at least one emitter of the array of emitters and at least one receiver of the array of receivers based on the quality of signal transmission between the various emitters and receivers.

2. The detector of claim 1, wherein the adjustment mechanism comprises a pivotable mount for holding the at least one emitter and at least one receiver so that the emitter and receiver maintain alignment with each other for a variety of conduit sizes.

3. The detector of claim 2, further comprising arms, wherein the mounts are pivotably attached to the arms, and wherein the arms are pivotable with respect to each other to thereby vary the distance between the at least one emitter and at least one receiver.

4. The detector of claim 1, wherein the at least one emitter and at least one receiver are slidably mounted to arms so as to slide along the length of the arms, and wherein the arms are pivotable with respect to each other to thereby vary the distance between the at least one emitter and at least one receiver.

5. The detector of claim 1, further comprising an alignment member disposed adjacent at least one of the at least one emitter and at least one receiver configured for holding a conduit between the at least one emitter and at least one receiver.

6. The detector of claim 5, wherein the alignment member comprises a notch formed adjacent at least one of the at least one emitter and at least one receiver.

7. The detector of claim 1, wherein the adjustment mechanism comprises a slide for allowing the at least one emitter and at least one receiver to slide towards and away from each other.

8. The detector of claim 1, wherein the at least one emitter and at least one receiver are biased towards each other.

9. The detector of claim 1, wherein the at least one emitter and at least one receiver may be locked at a fixed distance relative to each other.

10. The detector of claim 1, further comprising at least one circuit for determining the distance between the at least one emitter and at least one receiver.

11. The detector of claim 10, wherein the at least one circuit comprises a variable resistor.

* * * * *